United States Patent
Ben-Sasson et al.

(10) Patent No.: US 9,873,724 B2
(45) Date of Patent: Jan. 23, 2018

(54) PRO-ANGIOGENIC PEPTIDES AND PEPTIDE CONJUGATES

(71) Applicant: Yissum Research Development Company of the Hebrew University of Jerusalem Ltd., Jerusalem (IL)

(72) Inventors: Shmuel Ben-Sasson, Jerusalem (IL); Hadas Reuveni, Har Adar (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 0 days.

(21) Appl. No.: 15/105,762

(22) PCT Filed: Dec. 17, 2014

(86) PCT No.: PCT/IL2014/051104
§ 371 (c)(1),
(2) Date: Jun. 17, 2016

(87) PCT Pub. No.: WO2015/092792
PCT Pub. Date: Jun. 25, 2015

(65) Prior Publication Data
US 2016/0333070 A1 Nov. 17, 2016

Related U.S. Application Data

(60) Provisional application No. 61/919,039, filed on Dec. 20, 2013.

(51) Int. Cl.
| | | |
|---|---|---|
| A61K 38/00 | (2006.01) | |
| A61P 11/00 | (2006.01) | |
| C07K 14/705 | (2006.01) | |
| A61K 38/18 | (2006.01) | |
| A61K 38/19 | (2006.01) | |
| A61L 27/54 | (2006.01) | |
| A61L 31/16 | (2006.01) | |
| A61K 9/00 | (2006.01) | |
| A61K 47/34 | (2017.01) | |
| C07K 5/09 | (2006.01) | |
| C07K 5/10 | (2006.01) | |
| C07K 5/11 | (2006.01) | |
| C07K 7/06 | (2006.01) | |

(52) U.S. Cl.
CPC ............ C07K 14/705 (2013.01); A61K 9/008 (2013.01); A61K 9/0024 (2013.01); A61K 38/1816 (2013.01); A61K 38/1825 (2013.01); A61K 38/19 (2013.01); A61K 47/34 (2013.01); A61L 27/54 (2013.01); A61L 31/16 (2013.01); C07K 5/0817 (2013.01); C07K 5/10 (2013.01); C07K 5/1019 (2013.01); C07K 7/06 (2013.01); A61K 38/00 (2013.01); A61L 2300/25 (2013.01); A61L 2300/412 (2013.01); C07K 2319/033 (2013.01)

(58) Field of Classification Search
CPC ............ A61K 2300/00; A61K 38/1816; A61K 38/1825; A61K 38/19; A61K 38/00; A61K 47/34; A61K 9/0024; A61K 9/008; A61L 2300/25; A61L 2300/412; A61L 27/54; A61L 31/16; C07K 14/705; C07K 2319/033
See application file for complete search history.

(56) References Cited

U.S. PATENT DOCUMENTS

| | | | |
|---|---|---|---|
| 3,773,919 A | 11/1973 | Boswell et al. | |
| 5,391,377 A | 2/1995 | Barnwell | |
| 6,075,136 A | 6/2000 | Tang et al. | |
| 6,864,229 B2 | 3/2005 | Kuliopulos et al. | |
| 2005/0191240 A1* | 9/2005 | Srinivasan | A61K 47/48276 424/1.69 |
| 2007/0087977 A1* | 4/2007 | Robbins | A61K 31/195 514/23 |

FOREIGN PATENT DOCUMENTS

| | | | | |
|---|---|---|---|---|
| WO | WO93/00359 | * | 1/1993 | ............... C07K 7/08 |
| WO | WO9300359 | * | 1/1993 | ............... C07K 7/08 |
| WO | 95/33765 A1 | | 12/1995 | |
| WO | 01/81408 A2 | | 11/2001 | |
| WO | 2004/022576 A2 | | 3/2004 | |

OTHER PUBLICATIONS

Belikoff et al., (2011) A2B adenosine receptor blockade enhances macrophage-mediated bacterial phagocytosis and improves polymicrobial sepsis survival in mice. J Immunol 186(4): 2444-2453.
Benovic et al., (1990) Synthetic peptides of the hamster β2-adrenoceptor as substrates and inhibitors of the β-adrenoceptor kinase. Br J Clin Pharmacol 30(Suppl 1): 3S-12S.
Brissova et al., (2006) Pancreatic islet production of vascular endothelial growth factor—a is essential for islet vascularization, revascularization, and function. Diabetes 55(11): 2974-2985.
Christensson et al., (1990) Enzymatic activity of prostate-specific antigen and its reactions with extracellular serine proteinase inhibitors. Eur J Biochem 194(3): 755-763.
Doulut et al., (1992) Reduced peptide bond pseudopeptide analogues of neurotensin. Pept Res 5(1): 30-38.

(Continued)

*Primary Examiner* — Marcela M Cordero Garcia
(74) *Attorney, Agent, or Firm* — Vorys, Sater, Seymour and Pease LLP

(57) ABSTRACT

Short bioactive sequences derived from the $2^{nd}$ loop of the 7-transmembranal receptor of endothelial differentiation gene 3 (EDG3) useful in stimulation of angiogenesis, and peptide conjugates comprising a permeability enhancing moiety, are provided. Also provided are pharmaceutical compositions comprising the peptides and methods of use in conditions were insufficient blood-supply occurs, or which are associated with endothelia dysfunction such as peripheral vascular diseases, coronary artery diseases, cerebrovascular diseases, diabetes and delayed wound healing, pulmonary disease, eye diseases and pathological condition related to severe infection.

14 Claims, 5 Drawing Sheets

(56) References Cited

OTHER PUBLICATIONS

English et al., (2001) Platelet-released phospholipids link haemostasis and angiogenesis. Cardiovasc Res 49(3): 588-599.
Goto et al., (2006) Search for appropriate experimental methods to create stable hind-limb ischemia in mouse. Tokai J Exp Clin Med 31(3): 128-132.
Herbert et al., (1998) A large-scale process to produce microencapsulated proteins. Pharm Res 15(2): 357-361.
Johnson et al., (1996) A month-long effect from a single injection of microencapsulated human growth hormone. Nat Med 2(7): 795-799.
Keller et al., (2014) Calcitonin controls bone formation by inhibiting the release of sphingosine 1-phosphate from osteoclasts. Nat Commun 5: 5215; 13 pages.
Kenyon et al., (1996) A model of angiogenesis in the mouse cornea. Invest Ophthalmol Vis Sci 37(8): 1625-1632.
Licht et al., (2003) Induction of pro-angiogenic signaling by a synthetic peptide derived from the second intracellular loop of S1P3 (EDG3). Blood 102(6): 2099-107.
Nissanov et al., (1995) Automatic vessel segmentation and quantification of the rat aortic ring assay of angiogenesis. Lab Invest 73(5): 734-739.
O'Callaghan et al., (2012) Turning receptors on and off with intracellular pepducins: new insights into G-protein-coupled receptor drug development. J Biol Chem 287(16): 12787-12796.
Pillai et al. (2001) Polymers in drug delivery. Curr Opin Chem Biol 5(4): 447-451.
Rutherford et al., (1997) Recommended standards for reports dealing with lower extremity ischemia: revised version. J Vasc Surg 26(3): 517-538.
Severino et al., (2013) Identification of a pepducin acting as S1P3 receptor antagonist. J Pept Sci 19(11): 717-724.
Tracy (1998) Development and scale-up of a microsphere protein delivery system. Biotechnol Prog 14(1): 108-115.
Database WPI, week 199401; Thomson Scientific, London, GB; AN 1994-002154, XP002738167 & JP H05-306296 A, abstract (1993).
Database WPI, week 199429; Thomson Scientific, London, GB; AN 1994-238669, XP002738168 & JP H06-172212 A, abstract (1994).

* cited by examiner

PRO-ANGIOGENIC PEPTIDES AND PEPTIDE CONJUGATES

The Sequence Listing submitted in text format (.txt) filed on Jul. 13, 2016, named "SequenceListing.txt", created on Jun. 26, 2016, 18.9 KB), is incorporated herein by reference.

FIELD OF THE INVENTION

The present invention relates to short bioactive peptides derived from the $2^{nd}$ loop of the 7-transmembranal receptor of endothelial differentiation gene 3 (EDG3) useful in stimulation of angiogenesis and blood-vessel integrity, and peptide conjugates comprising a permeability enhancing moiety.

BACKGROUND OF THE INVENTION

One of the largest families of receptors in the human genome is that of the 7 transmembrane receptor (7-TMR) superfamily, also known as G-protein coupled receptors (GPCRs), numbering approximately 2000 proteins. G-protein coupled receptors regulate a large number of important physiological processes. At least 40% of the prescription drugs that have been developed have actions related to these receptors. Most of these drugs work by interfering with the ligand binding to the receptor that occurs outside of cells.

There is an ongoing effort in the scientific community to define compounds that block the intracellular interaction between the receptor and its signal transducing partner, the G-protein.

The second intracellular loop of the 7TMR receptors is known to play an important role in the signal transduction as mutations in this region cause a disturbance in the 7TMR-associated signal transduction. For example, there has been an attempt (Benovic et al., Br. J. Clin. Pharmac., 30:3s-12s, 1990) to interfere with the $\beta_2$-adrenoreceptor signal transduction by administration of peptides corresponding to the full second loop of this receptor. However, these results were extremely unsatisfactory.

Angiogenesis is an important natural process that occurs during embryogenesis, and in the adult healthy body in the process of wound healing, and results in restoration of blood flow back into injured tissues. In females, angiogenesis also occurs during the monthly reproductive cycle to build up the uterus lining and to support maturation of oocytes during ovulation, and in pregnancy when the placenta is formed, in the process of the establishment of circulation between the mother and the fetus. The healthy body controls angiogenesis through the interactions of angiogenesis-stimulating growth factors, and angiogenesis inhibitors, and the balance between the two determines whether angiogenesis is stimulated or inhibited.

In several therapeutic fields, there has been a growing interest in the control of angiogenesis. In one aspect, the aim is to control or diminish excessive and pathological angiogenesis that occurs in diseases such as cancer, diabetic blindness, age related macular degeneration, rheumatoid arthritis, psoriasis, and additional conditions. In these pathological conditions the new blood vessels feed the diseased tissue, for example the tumor tissue, providing it with essential oxygen and nutrients thus enabling its pathological growth. In some conditions the pathological angiogenesis many times destroys the normal tissue. Furthermore, the new blood vessels, formed for example in the tumor tissue, enable the tumor cells to escape into the circulation and metastasize in other organs. Typically, excessive angiogenesis occurs when diseased cells produce abnormal amounts of angiogenetic growth factors, overwhelming the effect of the natural angiogenesis inhibitors present in the body.

Anti-angiogenic therapies developed today are aimed at preventing new blood vessel growth through the targeting and neutralization of any of the stimulators that encourage the formation of new blood vessels.

Another aim of regulating angiogenesis is the stimulation of production of neovascularization in conditions were insufficient blood-supply occurs, leading to tissue ischemia. Typically, these conditions are diseases such as coronary artery diseases, peripheral artery diseases, stroke, and delayed wound healing (for example in ulcer lesions). In these conditions, when adequate blood vessel growth and circulation is not properly restored, there is a risk of tissue death due to insufficient blood flow. Typically, insufficient blood-supply occurs when the tissues do not produce adequate amounts of angiogenic growth-factors, and therapeutic angiogenesis is aimed at stimulating new blood vessels' growth by the use of growth factors or their mimics.

The main goal of the angiogenesis promoting therapy is to produce a biobypass—i.e. to physically bypass diseased or blocked arteries, by tricking the body into building new collateral blood vessels.

Sphingosine 1-phosphate (S1P) has been shown to be a major pro-angiogenic factor in the serum (English et al., Cardiovasc Res. 2001; 49:588-599). S1P is released from platelets on their activation and contributes to wound healing processes. Its production is catalyzed by sphingosine kinase, while degradation is either via cleavage to produce palmitaldehyde and phosphoethanolamine or by dephosphorylation. S1P serves as a key element in the angiogenic response by triggering proliferation and migration of endothelial cells as well as capillary morphogenesis, and stabilizing the new-formed endothelial capillary, by enhancing cell-cell contacts and recruiting smooth muscle cells. S1P can also bind to members of the endothelial differentiation gene (EDG) G-protein-coupled receptor family (namely EDG1 also known as S1P1, EDG3 also known as S1P3, EDG5 also known as H218, AGR16, or S1P2, EDG6 also known as S1P4 and EDG8 also known as S1P5) to elicit biological responses. These receptors are coupled differentially via G(i), G(q), G(12/13) and Rho to multiple effector systems, including adenylate cyclase, phospholipases C and D, extracellular-signal-regulated kinase, c-Jun N-terminal kinase, p38 mitogen-activated protein kinase and non-receptor tyrosine kinases. These signaling pathways are linked to transcription factor activation, cytoskeletal proteins, adhesion molecule expression, caspase activities, etc. Therefore sphingosine 1-phosphate can affect diverse biological responses, including mitogenesis, differentiation, migration and apoptosis, via receptor-dependent mechanisms. Additionally, S1P has been proposed to play an intracellular role, for example in Ca(2+) mobilization. Recently, it was shown (Keller et al., 2014 Nature Communications, 5, 5215) that S1P plays an important role in bone-formation in adults through S1P3 signaling.

The $2^{nd}$ loop of the 7 transmembranal receptor S1P3, also named EDG3 was shown to be involved in angiogenesis. Licht et al. 2003 (Blood, 102, 2099-2107) represented induction of pro-angiogenic signaling, and synergism with known angiogenic factors, by a nine-amino acid peptide having the sequence Myristyl-Gly-Met-Arg-Pro-Tyr-Asp-Ala-Asn-Lys-Arg (SEQ ID NO: 1) derived from the C-terminal end of the $2^{nd}$ loop of the EDG3 (residues 143-151). No shorter sequences are disclosed in this publication.

WO 01/81408 and its US counterpart, U.S. Pat. No. 6,864,229, disclose peptides and peptide conjugates derived from the third intracellular loop of certain G-protein coupled receptors (protease-activated receptor-1 (PAR1), PAR2, PAR4, CCKB, CCKA, SSTR2 and MC4). These documents do not provides sequence and/or activity of peptides derived from the second loop of G-protein coupled receptors, nor they disclose or suggest peptides or conjugates derived from the S1P3/EDG3 G-protein coupled receptor.

WO 2004/022576 suggests peptides and analogs, of at least five amino acids, derived from the $2^{nd}$ loop of the 7 transmembranal receptor EDG3, useful in stimulation of angiogenesis. Disclosed peptides contain at least 6 amino acids of the native sequence, or are analogs of these peptides, for example the compound Nle-Arg-Pro-Tyr-Asn-Ala (SEQ ID NO:2), derived from the sequence Met-Arg-Pro-Tyr-Asp-Ala (SEQ ID NO:3) of the native EDG3 sequence. Long peptide sequences are not optimal as therapeutic agents due to their flexible conformation, which affects activity and selectivity, and they comprise more cleavage sites for peptidases.

U.S. Pat. No. 6,075,136 related to human prostate-associated serine protease (PRASP) describes an assay for measuring PRASP activity which measures the hydrolysis of the synthetic peptide methyl-O-succinyl-Arg-Pro-Tyr-NH-p-nitroanilide that serves as a universal substrate for chymotrypsin-like serine proteases, including PSA (Christensson, A. et al. 1990, Eur. J. Biochem. 194:755-763).

There is therefore an unmet need for providing improved peptides which are more appropriate as drug candidates for stimulation of angiogenesis in conditions were insufficient blood-supply occurs.

SUMMARY OF THE INVENTION

The present invention provides for the first time short synthetic peptides and peptide conjugates useful for stimulation of blood vessel growth and for improving cases of endothelial dysfunction in particular endothelial dysfunction associated with excessive leakiness. The peptides provided are candidates as therapeutic agents for treatment of vascular disorders in which blood vessel growth is desirous, such as peripheral vascular disease, myocardial ischemia, peripheral artery diseases, tissue graft, and diabetes and for other disorders and conditions mediated through a sphingosine 1-phosphate (S1P) receptor.

It is now disclosed that novel peptides sharing only three amino acids homologous with the sequence of the intracellular $2^{nd}$ loop 7-transmembranal receptor endothelial differentiation gene-3 (EDG3), are effective in stimulating angiogenesis and act synergistically with other angiogenesis stimulators in stimulating angiogenesis.

The present invention provides, according to one aspect, a peptide of 3-10 amino acids comprising the core sequence RPY, wherein R is an arginine residue or a modified arginine residue, P is a proline residue or a modified proline residue, Y is a tyrosine residue or a modified tyrosine residue, wherein said peptide shares no more than three amino acids that are identical to those of the corresponding residues 143-147 of endothelial differentiation gene receptor 3 (EDG3), having the sequence Met-Arg-Pro-Tyr-Asp (SEQ ID NO: 4).

According to some embodiments, the peptide consists of 3-9 amino acids.

According to yet other embodiments, the peptide consists of 4-8 amino acids.

According to some specific embodiments, the peptide consists of 4, 5 or 6 amino acids. Each possibility represents a separate embodiment of the present invention.

According to one embodiment the peptide is capable of promoting the growth of blood vessels. According to a specific embodiment the peptide is capable of stimulating angiogenesis. According to another embodiment the peptide is capable of improving endothelial function, in particular decreasing leakiness of dysfunctional endothelia.

According to one embodiment, the peptide further comprises a permeability-enhancing moiety covalently connected to said peptide via a direct bond or via a linker, to form a peptide conjugate. The permeability-enhancing moiety according to the present invention may be connected to any free group of the active peptide.

According to some embodiments, the linker consists of 1-5 amino acid residues.

According to some specific embodiments the linker consists of a glycine residue.

According to some specific embodiments the permeability moiety is a fatty acid and the linker is a glycine residue.

According to another some embodiments the RPY sequence is selected from the group consisting of:
Arg-Pro-Tyr;
Arg-Pro-35dITyr;
hArg-Pro-Tyr;
hArg-Pro-35dITyr and
hArg-4Hyp-Tyr;
wherein hArg is homoarginine, 35dITyr is 3,5-diiodotyrosine and 4Hyp is 4hydroxyproline. Each possibility represents a separate embodiment of the present invention.

According to other embodiments, the present invention provides a peptide conjugate according to Formula I:

Z—X—R—P—Y—B        (Formula I)

wherein Z designates a moiety capable of increasing permeability covalently connected via a direct bond or via a linker, X designates a natural or synthetic amino acid residue other than methionine or X may be absent, R is an arginine residue or a modified R residue, P is a proline residue or a modified proline residue, Y is a tyrosine residue or a modified tyrosine residue, and B designates a terminal carboxy acid, amide, ester or alcohol group.

According to some embodiments the peptide in the peptide-conjugate is selected from the group consisting of:

| | |
|---|---|
| Gly-Arg-Pro-Tyr-B; | (SEQ ID NO. 5) |
| Gly-Nle-Arg-Pro-Tyr-B; | (SEQ ID NO. 6) |
| Gly-Nle-Arg-Pro-35dITyr-B; | (SEQ ID NO. 7) |
| Gly-Nle-hArg-Pro-Tyr-B; | (SEQ ID NO. 8) |
| Gly-Nle-hArg-Pro-35dITyr-B; and | (SEQ ID NO. 9) |
| Gly-Nle-hArg-4HyP-Tyr. | (SEQ ID NO. 10) |

Each possibility represents a separate embodiment of the present invention.

According to some embodiments, the linker consists of 1-5 amino acid residues.

According to some specific embodiments X is a norleucine (Nle) residue.

Non limiting examples for a modified arginine residue are: homoarginine (hArg), N-Methyl arginine (NMeArg), citruline, 2-amino-3-guanidinopropionic acid, N-imino-ethyl-L-ornithine, Nω-monomethyl-L-arginine, Nω-nitro-L- arginine, D-arginine, 2-amino-3-ureidopropionic acid, Nω,ω-dimethyl-L-arginine, Nω-Nitro-D-arginine. Each possibility represents a separate embodiment of the present invention.

Non limiting examples for a modified proline residue are: homoproline (hPro), (4-hydroxy)Pro (4HyP), (3-hydroxy)Pro (3HyP), gamma-benzyl-proline, gamma-(2-fluoro-benzyl)-proline, gamma-(3-fluoro-benzyl)-proline, gamma-(4-fluoro-benzyl)-proline, gamma-(2-chloro-benzyl)-proline, gamma-(3-chloro-benzyl)-proline, gamma-(4-chloro-benzyl)-proline, gamma-(2-bromo-benzyl)-proline, gamma-(3-bromo-benzyl)-proline, gamma-(4-bromo-benzyl)-proline, gamma-(2-methyl-benzyl)-proline, gamma-(3-methyl-benzyl)-proline, gamma-(4-methyl-benzyl)-proline, gamma-(2-nitro-benzyl)-proline, gamma-(3-nitro-benzyl)-proline, gamma-(4-nitro-benzyl)-proline, gamma-(1-naphthalenylmethyl)-proline, gamma-(2-naphthalenylmethyl)-proline, gamma-(2,4-dichloro-benzyl)-proline, gamma-(3,4-dichloro-benzyl)-proline, gamma-(3,4-difluoro-benzyl)-proline, gamma-(2-trifluoro-methyl-benzyl)-proline, gamma-(3-trifluoro-methyl-benzyl)-proline, gamma-(4-trifluoro-methyl-benzyl)-proline, gamma-(2-cyano-benzyl)-proline, gamma-(3-cyano-benzyl)-proline, gamma-(4-cyano-benzyl)-proline, gamma-(2-iodo-benzyl)-proline, gamma-(3-iodo-benzyl)-proline, gamma-(4-iodo-benzyl)-proline, gamma-(3-phenyl-allyl-benzyl)-proline, gamma-(3-phenyl-propyl-benzyl)-proline, gamma-(4-tert-butyl-benzyl)-proline, gamma-benzhydryl-proline, gamma-(4-biphenyl-methyl)-proline, gamma-(4-thiazolyl-methyl)-proline, gamma-(3-benzothienyl-methyl)-proline, gamma-(2-thienyl-methyl)-proline, gamma-(3-thienyl-methyl)-proline, gamma-(2-furanyl-methyl)-proline, gamma-(2-pyridinyl-methyl)-proline, gamma-(3-pyridinyl-methyl)-proline, gamma-(4-pyridinyl-methyl)-proline, gamma-allyl-proline, gamma-propynyl-proline, alpha-modified-proline residues, pipecolic acid, azetidine-3-carboxylicacid. Each possibility represents a separate embodiment of the present invention.

Non limiting examples for a modified tyrosine residue are: 3,5 diiodotyrosine (35dITyr), 3,5 diBromotyrosine (35dBTyr), homotyrosine, D-tyrosine, 3-amino-L-tyrosine, 3-amino-D-tyrosine, 3-iodo-L-tyrosine, 3-iodo-D-tyrosine, 3-methoxy-L-tyrosine, 3-methoxy-D-tyrosine, L-thyroxine, D-thyroxine, L-thyronine, D-thyronine, O-methyl-L-tyrosine, O-methyl-D-tyrosine, D-thyronine, O-ethyl-L-tyrosine, O-ethyl-D-tyrosine, 3,5,3'-triiodo-L-thyronine, 3,5,3'-triiodo-D-thyronine, 3,5-diiodo-L-thyronine, 3,5-diiodo-D-thyronine, D-meta-tyrosine, L-meta-tyrosine, D-ortho-tyrosine, L-ortho-tyrosine, phenylalanine, substituted phaenylalanine, N-nitro phenylalanine, p-nitro phenylalanine. Each possibility represents a separate embodiment of the present invention.

According to a specific embodiment Z is Myristoyl-glycine (Myr-Gly), X is norleucine (Nle), R is selected from the group consisting of an arginine residue, an homoarginine residue (hArg), an Nα-methyl arginine residue (NMeArg), a citruline residue, a 2-amino-3-guanidinopropionic acid residue; P is a proline residue or 4 hydroxy proline residue (4HyP), and Y is selected from the group consisting of: a tyrosine residue, a 3,5 diiodo tyrosine residue (35dITyr), a 3,5 diBromotyrosine residue (35dBTyr), and an homotyrosine residue. Each possibility represents a separate embodiment of the present invention.

According to some embodiments the peptide conjugate is selected from the group consisting of:

| | |
|---|---|
| Myr-Gly-Arg-Pro-Tyr-NH$_2$; | (SEQ ID NO: 11) |
| Myr-Gly-Nle-Arg-Pro-Tyr-NH$_2$; | (SEQ ID NO: 12) |

-continued

| | |
|---|---|
| Myr-Gly-Nle-Arg-Pro-35dITyr-NH$_2$; | (SEQ ID NO: 13) |
| Myr-Gly-Nle-hArg-Pro-Tyr-NH$_2$; | (SEQ ID NO: 14) |
| Myr-Gly-Nle-hArg-Pro-35dITyr-NH$_2$; and | (SEQ ID NO: 15) |
| Myr-Gly-Nle-hArg-4HyP-Tyr. | (SEQ ID NO: 16) |

Each possibility represents a separate embodiment of the present invention.

According to a specific embodiment, a pro angiogenesis peptide conjugate is provided consisting of a cell-permeability enhancing moiety covalently connected, through an optional linker, to a sequence comprising the core sequence RPY, wherein R is an arginine residue or a modified arginine residue, P is a proline residue or a modified proline residue, Y is a tyrosine residue or a modified tyrosine residue, wherein said peptide shares no more than three amino acids that are identical to those of corresponding residues 143-147 of EDG3.

Previously disclosed peptides derived from EDG3 are at least 6 amino acids long and contain at least 5 residues which are identical or homologous to the native EDG3 sequence. The shortest known peptide is the peptide R002L106 having the sequence Nle-<u>Arg</u>-<u>Pro</u>-<u>Tyr</u>-Asn-<u>Ala</u> (SEQ ID NO: 2), which contain in four of its six positions residues (underlined) identical to those of the native EDG3 sequence Met-Arg-Pro-Tyr-Asp-Ala (SEQ ID NO:3), and one which is a conservative substitution (asparagine instead of aspartic acid, italic) of the residue present in the native sequence. The EDG3 derived sequences of the present invention are shorter and contain no more than three contiguous residues identical or homologous to the native sequence. It was now unexpectedly found that the core sequence responsible for the angiogenesis activity is the Arg-Pro-Tyr sequence, and that peptides according to the present invention, which are shorter than previously known peptides, are more active than longer sequences which have higher homology to the native sequence from which they are derived.

According to specific embodiments, a peptide conjugate is provided comprising the core sequence RPY, wherein R is an arginine residue or a modified arginine residue, P is a proline residue or a modified proline residue, Y is a tyrosine residue or a modified tyrosine residue, further comprising a permeability-enhancing moiety coupled through an optional linker to the peptide.

According to some embodiments, the active peptides are conjugated to the tripeptide Asp-Arg-Tyr, or to a homologous sequence.

According to some embodiments the amino terminus of the peptide is modified, e.g., it may be acylated. According to additional embodiments the carboxy terminus is modified, e.g., it may be acylated, amidated, reduced or esterified.

It is to be explicitly understood that previously known peptides are excluded from the present invention.

Cyclic versions of the peptides disclosed herein are also within the scope of the present invention.

Any moiety known in the art to facilitate actively or passively or enhance permeability of the compound into cells may be used for conjugation with the peptide core according to the present invention. Non-limitative examples include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides. According to a preferred embodiment, the hydrophobic moiety is a lipid moiety or an amino acid moiety.

The permeability-enhancing moiety may be connected to any position in the peptide moiety, directly or through a spacer or linker, preferably to the amino terminus of the peptide moiety.

It is yet another object of the present invention to provide blood-vessel promoting and angiogenesis stimulating peptides and conjugates comprising peptidomimetic compounds having further improved stability and cell permeability properties. Non limiting examples of such compounds include N-alkylation of selected peptide residues, side-chain modifications of selected peptide residues, non-natural amino acids, use of carbamate, urea, sulfonamide and hydrazine for peptide bond replacement, and incorporation of non-peptide moieties including but not limited to piperidine, piperazine and pyrrolidine, through a peptide or non-peptide bond. Modified bonds between amino acid residues in peptidomimetics according to the present invention may be selected from the group consisting of: an amide, urea, carbamate, hydrazine or sulfonamide bond. Unless explicitly stated otherwise the bonds between the amino acid residues are all amide bonds.

According to some embodiments, a peptide or a peptide conjugate according to the present invention comprises at least one non-natural encoded amino acid residue.

According to some specific embodiments the at least one non-natural amino acid residue is selected from the group consisting of: Norleucine (Nle), modified Arginine (Arg), modified Proline (Pro) and modified Tyrosine (Tyr).

According to some embodiments, at least one residue of the core sequence RPY is a non-natural encoded amino acid residue or a modified residue.

According to other embodiments, a peptide conjugate according to the present invention comprises at least one non-natural permeability-enhancing moiety.

In another aspect, the present invention provides a pharmaceutical composition comprising as an active ingredient at least one peptide or peptide-conjugate defined above, further comprising a pharmaceutically acceptable excipient, diluent or carrier.

According to some embodiments the RPY sequence is selected from the group consisting of:
  Arg-Pro-Tyr;
  Arg-Pro-Tyr;
  Arg-Pro-35dITyr;
  hArg-Pro-Tyr;
  hArg-Pro-35dITyr; and
  hArg-4Hyp-Tyr.

According to other embodiments the pharmaceutical composition comprises a peptide selected from the group consisting of:

| | |
|---|---|
| Gly-Arg-Pro-Tyr-NH$_2$; | (SEQ ID NO. 5) |
| Gly-Nle-Arg-Pro-Tyr-NH$_2$; | (SEQ ID NO. 6) |
| Gly-Nle-Arg-Pro-35dITyr-NH$_2$; | (SEQ ID NO. 7) |
| Gly-Nle-hArg-Pro-Tyr-NH$_2$; | (SEQ ID NO. 8) |
| Gly-Nle-hArg-Pro-35dITyr-NH$_2$; and | (SEQ ID NO. 9) |
| Gly-Nle-hArg-4HyP-Tyr. | (SEQ ID NO. 10) |

Each possibility represents a separate embodiment of the present invention.

According to one embodiment, the peptide contained in the pharmaceutical composition comprises a permeability-enhancing moiety covalently connected to said peptide via a direct bond or via a linker, to form a peptide conjugate, a pharmaceutically acceptable carrier.

According to a specific embodiment the permeability-enhancing moiety is a fatty acid and the linker is a stretch of 1-12 amino acid residues.

According to some specific embodiments the linker consists of a glycine residue.

According to another embodiment, a pharmaceutical composition comprising a peptide conjugate according to Formula I is provided:

Z—X—R—P—Y—B (Formula I)

wherein Z designates a moiety capable of increasing permeability covalently connected via a direct bond or via a linker, X designates a natural or synthetic amino acid residue other than methionine, or X may be absent, R is an arginine residue or a modified R residue, P is a proline residue or a modified proline residue, Y is a tyrosine residue or a modified tyrosine residue, and B designates a terminal carboxy acid, amide, ester or alcohol group.

According to a specific embodiment X is a norleucine residue.

According to a specific embodiment Z is Myristoyl-glycine (Myr-Gly), X is norleucine (Nle), R is selected from the group consisting of an arginine residue, an homoarginine residue (hArg), an N-methylarginine residue (NMeArg), a citruline residue, a 2-amino-3-guanidinopropionic acid residue; P is a proline residue or 4 hydroxy proline residue (4Hyp) and Y is selected from the group consisting of: a tyrosine residue, a 3,5 diiodo tyrosine residue (35dITyr), a 3,5 diBromo tyrosine residue (35dBTyr), and an homotyrosine residue.

According to some embodiments the peptide conjugate in the pharmaceutical composition is selected from the group consisting of:

| | |
|---|---|
| Myr-Gly-Arg-Pro-Tyr-NH$_2$; | (SEQ ID NO. 11) |
| Myr-Gly-Nle-Arg-Pro-Tyr-NH$_2$; | (SEQ ID NO. 12) |
| Myr-Gly-Nle-Arg-Pro-35dITyr-NH$_2$; | (SEQ ID NO. 13) |
| Myr-Gly-Nle-hArg-Pro-Tyr-NH$_2$; | (SEQ ID NO. 14) |
| Myr-Gly-Nle-hArg-Pro-35dITyr-NH$_2$; and | (SEQ ID NO. 15) |
| Myr-Gly-Nle-hArg-4HyP-Tyr. | (SEQ ID NO. 16) |

Each possibility represents a separate embodiment of the present invention.

A pharmaceutical composition according to some embodiments of the present invention comprises a pharmaceutically acceptable carrier aimed to improve stability, solubility, permeability or to provide a specific, prolonged or modified release of at least one active ingredient.

According to some embodiments, the carrier is suitable for administration by inhalation.

According to some embodiment, a formulation according to the invention for administration by inhalation is selected from the group consisting of liposomal formulation, dry-powder formulation, suspension formulation, solution formulation, metered dose inhaler formulation and nebulizer formulation.

According to some embodiments the formulation for inhalation comprises at least one of: a surfactant, a propellant and a co-solvent.

According to some specific embodiments, the inhalation formulation comprises at least one surfactant.

According to some specific embodiments, the inhalation formulation comprises nanoparticles.

According to some embodiments, the formulation for inhalation comprises particles of less than 5 μm diameter, in order to reach bronchial regions.

According to some specific embodiments, the dry-powder formulation comprises lactose.

According to other embodiments, a modified-release pharmaceutical composition is provided comprising a peptide according to the invention and at least one carrier.

According to some embodiments, the modified-release pharmaceutical composition is in a form selected from the group consisting of: biodegradable microspheres, non-biodegradable microspheres, implants of any suitable geometric shape, implantable rods, implantable capsules, implantable rings, or prolonged release gels or erodible matrices.

The pharmaceutical composition may be administered alone or together with other angiogenesis stimulators, such as vascular endothelial growth factor (VEGF), fibroblast growth factor (FGF) and stem cell factor (SCF).

The pharmaceutical compositions of the present invention are useful for treating conditions in which insufficient blood-supply occurs or in diseases and/or pathological conditions wherein one of the causes or manifestation is dysfunctional endothelia, especially endothelia featuring excessive leakiness, or wherein signaling through S1P receptor is involved, such as bone formation in adults.

In accordance with the present invention, at least one peptide or peptide conjugate, derived from the $2^{nd}$ loop of endothelial differentiation gene receptor 3 (EDG3), comprising the core sequence RPY, wherein R is an arginine residue or a modified arginine residue, P is a proline residue or a modified proline residue, Y is a tyrosine residue or a modified tyrosine residue, wherein the peptide does not comprise additional residues identical to residues present at the same positions of said $2^{nd}$ loop of EDG3, is used for the preparation of a therapeutic medicament for prevention or treatment of a condition in which insufficient blood-supply occurs, in pathological conditions wherein one of the causes or manifestation is dysfunctional endothelia, especially endothelia featuring excessive leakiness, or in conditions wherein S1P is involved, such as bone formation in adults.

In accordance with the present invention, at least one peptide or peptide conjugate, derived from the $2^{nd}$ loop of endothelial differentiation gene receptor 3 (EDG3), comprising the core sequence RPY, wherein R is an arginine residue or a modified arginine residue, P is a proline residue or a modified proline residue, Y is a tyrosine residue or a modified tyrosine residue, wherein the peptide does not comprise additional residues identical to residues present at the same positions of said $2^{nd}$ loop of EDG3, is used in prevention or treatment of a disease or condition in which insufficient blood-supply occurs or in conditions wherein S1P signaling is involved. Specifically, peptides and peptide conjugates according to the invention are useful in promoting blood-vessel growth or endothelia function improving.

According to a specific embodiment the disease or condition is resulted or caused by dysfunctional endothelia.

According to other embodiments, the condition involved bone loss. According to some specific embodiments, the condition is osteoporosis.

According to some specific embodiments the disease or condition is selected from the group consisting of: peripheral vascular disease, ischemic diseases including but not limited to myocardial ischemia, tissue graft, coronary artery diseases, stroke, delayed wound healing, pulmonary disease including acute lung injury (ALI), acute respiratory distress syndrome (ARDS), and ventilation induced ling injury (VILI), eye diseases including age-related macular disease (AMD) and pathological condition related to severe infection such as for example sepsis. Each possibility represents a separate embodiment of the present invention.

According to some embodiments, a peptide or peptide conjugate according to the invention for use in prevention or treatment of septic shock is provided.

According to other embodiments the disease or condition are characterized by insufficient pancreatic beta cell function.

According to yet another embodiment the disease or condition to be prevented, ameliorated or treated is diabetes or pancreatic islet transplantation.

According to certain specific embodiments, the pharmaceutical composition of the invention is provided in a drug-eluting stent used for prevention or treatment of myocardial ischemia or coronary artery disease. Each possibility represents a separate embodiment of the present invention.

The invention further relates to a method for the prevention or treatment of conditions in which insufficient blood-supply occurs, where the endothelial function deteriorates, or wherein conditions mediated through S1P receptor signaling, said method comprising administering to a subject in need thereof a therapeutically effective amount of a pharmaceutical composition according to the invention.

According to a specific embodiments the disease or condition in which insufficient blood-supply occurs or where the endothelial function deteriorates, is selected from the group consisting of: peripheral vascular disease, myocardial ischemia, tissue graft, coronary artery diseases, stroke, diabetes, pancreatic islet transplantation and delayed wound healing, pulmonary disease including acute lung injury (ALI), acute respiratory distress syndrome (ARDS), and ventilation induced ling injury (VILI), eye diseases including age-related macular disease (AMD) and pathological condition related to severe infection such as for example sepsis. Each possibility represents a separate embodiment of the present invention.

According to some embodiments, the condition mediates through S1P receptor involved bone loss. According to some specific embodiments, the condition is osteoporosis.

According to some embodiments, a method of preventing or treating septic shock is provided comprising administering a pharmaceutical composition according to the invention to a subject in need thereof.

According to another aspect of the present invention, a stent comprising a pharmaceutical composition according to the invention is provided.

A stent comprising a pharmaceutical composition according to the invention, for of prevention or treatment of myocardial ischemia or coronary artery disease is also provided.

Also included in the present invention are methods of prevention or treatment of myocardial ischemia or coronary artery disease, comprising administering to a subject in need thereof a stent according to the present invention.

Further embodiments and the full scope of applicability of the present invention will become apparent from the detailed description given hereinafter. However, it should be understood that the detailed description and specific examples,

DETAILED DESCRIPTION OF THE INVENTION

Figure 1A:
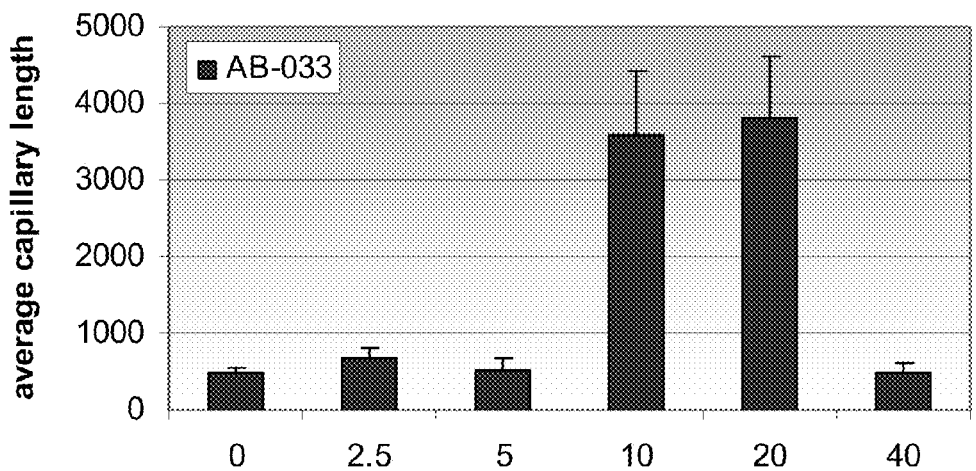
FIGS. 1A-1C show an induction of capillary formation in aortic ring assay by the peptides of SEQ ID NOs: 13 (FIG. 1A), 14 (FIG. 1B), and 12 (FIG. 1C), as determined by aortic ring capillary length.

As a result of major advances in organic chemistry and in molecular biology, many bioactive peptides can now be prepared in quantities sufficient for pharmacological and clinical use. Thus in the last few years new methods have been established for the treatment and diagnosis of illnesses in which peptides have been implicated. However, the use of peptides as therapeutic and diagnostic agents is limited by the following factors: a) tissue penetration; b) low metabolic stability towards proteolysis in the gastrointestinal tract and in serum; c) poor absorption after oral ingestion, in particular due to their relatively high molecular mass or the lack of specific transport systems or both; d) rapid excretion through the liver and kidneys; and e) undesired side effects in non-target organ systems, since peptide receptors can be widely distributed in an organism. The present invention provides bioactive peptides that: a) have improved tissue penetration due to their small size and the optional permeability moiety; b) have improved metabolic stability due to the blocked terminals and to incorporation of non-natural amino acids; c) have improved absorption due to their low molecular mass and the optional permeability moiety; d) are easier and cheaper to produce due to their low molecular mass and short sequence; and e) are expected to be selective to the EDG3 receptor from which they derive and therefore are expected to have less side effects.

As presented in table 1, previously disclosed peptides derived from EDG3 are at least 6 amino acids long and contain at least 5 residues which are identical or homologous to the native EDG3 sequence. The shortest known peptide is the peptide R002L106 (725-106, SEQ ID NO: 2) which contain in four of its six positions residues identical to those of the native sequence and one which is a conservative substitution (asparagine instead of aspartic acid) of the residue present in the native sequence. Some of the EDG3 derived sequences of the present invention, are only 4 amino acids long and contain in no more than three positions residues identical or homologous to the native sequence. It is unexpected that these sequences which are at least 30% shorter are more active than longer sequences which have higher homology to the native sequence from which they are derived.

TABLE 1

| Native EDG3 | | | | | | | | | | | SEQ ID No. |
|---|---|---|---|---|---|---|---|---|---|---|---|
| | Ile | Lys | Met | Arg | Pro | Tyr | Asp | Ala | Asn | Lys | Arg | 17 |
| A. Previously disclosed sequences | | | | | | | | | | | |
| R002L103 | | | Met | Arg | Pro | Tyr | Asp | Ala | Asn | Lys | Arg | 18 |
| R002L106 (725-106) | | | Nle | Arg | Pro | Tyr | Asn | Ala | | | | 2 |
| B. New sequences | | | | | | | | | | | |
| | | | Nle | Arg | Pro | Tyr | | | | | | 19 |
| | | | Nle | Arg | Pro | 35dITyr | | | | | | 20 |
| | | | Nle | hArg | Pro | Tyr | | | | | | 21 |
| | | | Nle | hArg | Pro | 35dITyr | | | | | | 22 |
| | | | Nle | hArg | 4HyP | Tyr | | | | | | 23 |

Nle is a norleucine residue,
hArg designates an homoarginine residue,
4HyP designates a 4-hydroxyproline residue, and
35dITyr designates a 3,5-diiodotyrosine residue.

According to a specific embodiment of the present invention, the new sequences presented in part B of table 1 serves as the basis for novel molecules disclosed in the present application, further containing a cell-permeability moiety coupled through an optional spacer to the peptide, preferably to the peptide's N-terminus.

Without wishing to be bound to a theory, the peptides of the present invention, comprising sequences sharing only three amino acids homology with the sequence of the EDG3 receptor, mimic the effects of sphingosine-1-phosphate (S1P), the natural ligand of S1P3 (EDG3) by triggering a Gi-dependent signal transduction while inhibiting G12/13 signaling. It is hypothesized that the G-protein inhibitor Pertusis toxin inhibits angiogenesis induced by the peptides of the present invention.

It is now shown by ex-vivo (sprouting of blood vessels from mouse aortic rings embedded in collagen matrix) and in-vivo experiments (mouse ischemic hind limb assay), that peptides according to the invention induce the formation of multi-layered and mature vessels. The results demonstrate that these peptides synergize with endogenous protein angiogenic factors (like VEGF,) and stimulate the formation of mature and stable blood vessels in contrast to VEGF tested alone under the same conditions. Since the levels of protein angiogenic factors like VEGF increase at the ischemic regions, it is provided that administration of the peptide of the invention as a monotherapy will yield the desirable angiogenic effect in situ, by synergizing with locally secreted endogenous factors.

In addition, it is now shown that peptides according to the invention, prevents blood-vessel leakiness in-vivo. The results demonstrate that these peptides enhance blood vessel integrity and inhibit macromolecules escape to the interstitial fluid.

The peptides of the present invention are preferably synthesized using conventional synthesis techniques known in the art, e.g., by chemical synthesis techniques including peptidomimetic methodologies. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984). A skilled artesian may synthesize any of the peptides of the present invention by using an automated peptide synthesizer using standard chemistry such as, for example, t-Boc or Fmoc chemistry. Synthetic peptides can be purified by preparative high performance liquid chromatography (Creighton T. 1983, Proteins, structures and molecular principles. WH Freeman and Co. N.Y.), and the composition of which can be confirmed via amino acid sequencing. Some of the peptides of the invention, which include only natural, namely genetically encoded, amino acids, may further be prepared using recombinant DNA techniques known in the art. The conjugation of the peptidic and permeability moieties may be performed using any methods known in the art, either by solid phase or solution phase chemistry. Some of the preferred compounds of the present invention may conveniently be prepared using solution phase synthesis methods. Other methods known in the art to prepare compounds like those of the present invention can be used and are comprised in the scope of the present invention.

Cyclic versions of the peptides disclosed herein are also within the scope of the present invention. Cyclization of peptides may take place by any means known in the art, for example through free amino and carboxylic groups present in the peptide sequence, or through amino acids or moieties added for cyclization. Non limiting examples of cyclization types are: side chain to side chain cyclization, C-to-N terminal cyclization, side chain to terminal cyclization, and any type of backbone cyclization incorporating at least one $N^{\alpha}$-$\omega$-substituted amino acid residue/s as described for example in WO 95/33765.

The permeability-enhancing moiety of the conjugates of the present invention may be connected to any position in the peptide moiety, directly or through a spacer. According to a specific embodiment, the cell-permeability moiety is connected to the amino terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

Definitions

For convenience and clarity certain terms employed in the specification, examples and claims are described herein.

The term "peptide" as used herein is meant to encompass natural (genetically encoded), non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, either the L or D isomers may be used.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, affinity to the target protein, metabolic stability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another.
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), methionine (M), Valine (V); and
6) Phenylalanine (F), Tyrosine (Y), Tryptophan (W).

Also included within the scope of the invention are salts of the peptides, analogs, and chemical derivatives of the peptides of the invention.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

A "chemical derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "peptide analog" indicates molecule which has the amino acid sequence according to the invention except for one or more amino acid changes or one or more modification/replacement of an amide bond. Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

"A peptide conjugate" according to the present invention, denotes a molecule comprising a sequence of a blood-vessel promoting peptide to which another moiety, either peptidic or non peptidic, is covalently bound, directly or via a linker.

The term "linker" denotes a chemical moiety, a direct chemical bond of any type, or a spacer whose purpose is to link, covalently, a cell-permeability moiety and a peptide or peptidomimetic. The spacer may be used to allow distance between the permeability-enhancing moiety and the peptide.

"Permeability" refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides, nanoparticles and liposomes.

The hydrophobic moiety according to the invention may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3)_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds.

Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene)ethylenediamine tetraiodide; N,N"-Bis(hexadecylaminocarbonylmethylene)-N,N',N"-tris((-N,N,N-trimethylammonium-ethylaminocarbonylmethyl-enediethylenetri amine hexaiodide; N,N'-Bis(dodecylaminocarbonylmethylene)-N,N"-bis((-N,N,N-trimethylammonium ethylaminocarbonylmethylene) cyclohexylene-1,4-diamine tetraiodide; 1,7,7-tetra-((-N,N,N,N-tetramethylammoniumethylamino-carbonylmethylene)-3-hexadecylaminocarbonylmethylene-1,3,7-triaazaheptane heptaiodide; N,N,N',N'-tetra((-N,N,N-trimethylammonium-ethylaminocarbonylmethylene)-N'-(1,2-dioleoylglycero-3-phosphoethanolamino carbonylmethylene)diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl) carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

The term "blood vessel growth" refers both to the processes of "angiogenesis" and "arteriogenesis".

The term "angiogenesis" (also referred to at times as "neovascularization") is a general term used to denote the growth of new blood vessels both in normal and pathological conditions.

The term "physiologically acceptable carrier" or "diluent" or "excipient" refers to an aqueous or non-aqueous fluid that is well suited for pharmaceutical preparations. Furthermore, the term "a pharmaceutically acceptable carrier or excipient" refers to at least one carrier or excipient and includes mixtures of carriers and or excipients. The term "therapeutic" refers to any pharmaceutical, drug or prophylactic agent which may be used in the treatment (including the prevention, diagnosis, alleviation, or cure) of a malady, affliction, disease or injury in a patient.

Pharmacology

Apart from other considerations, the fact that the novel active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes novel methods are being used, in order to design and provide metabolically stable and oral bioavailable peptidomimetic analogs.

The pharmaceutical composition of this invention may be administered by any suitable means, such as orally, topically, intranasally, subcutaneously, intramuscularly, intravenously, intra-arterially, intraarticulary, intralesionally, by inhalation or parenterally, and are specifically formulated for the administration route. Ordinarily, parenteral administration or administration by inhalation will be preferred and the compositions will be formulated accordingly.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., Curr. Opin. Chem. Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

In case of myocardial ischemia and coronary artery diseases, a preferred method for the prevention and/or treatment of such conditions would be the incorporation of the therapeutic peptide into a drug-eluting stent. Stents are being widely used to treat such conditions and the coating of stents with drug-containable polymers is well known to a person versed in the art. The local release of the therapeutic peptide according to the present invention, via a drug-eluting stent, might be advantageous due to the high concentration achieved at the desired site of the myocardium while the systemic concentration can become negligible.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

The preferred doses for administration of such pharmaceutical compositions range from about 0.1 µg/kg to about 20 mg/kg body weight. Preferably, the amount of the active ingredient is in the range of from about 10 to 5000 µg/kg.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In certain embodiments, peptide delivery can be enhanced by the use of protective excipients. This is typically accomplished either by complexing the peptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy, 1998, Biotechnol. Prog. 14, 108; Johnson et al., 1996, Nature Med. 2, 795; Herbert et al., 1998, Pharmaceut. Res. 15, 357) a dry powder composed of biodegradable polymeric microspheres containing the protein in a polymer matrix that can be compounded as a dry formulation with or without other agents.

In certain embodiments, dosage forms of the compositions of the present invention include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); poly-anhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}) methane), CPM; poly(p-{carboxyphenoxy}propane), CPP; poly(p-{carboxyphenoxy}hexane)s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8, 10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); poly-hydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) triblock copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment.

Depot Systems

The parenteral route by intravenous (IV), intramuscular (IM), or subcutaneous (SC) injection is the most common and effective form of delivery for small as well as large molecular weight drugs. However, pain, discomfort and inconvenience due to needle sticks makes this mode of drug delivery the least preferred by patients. Therefore, any drug delivery technology that can at a minimum reduce the total number of injections is preferred. Such reductions in frequency of drug dosing in practice may be achieved through the use of injectable depot formulations that are capable of releasing drugs in a slow but predictable manner and consequently improve compliance. For most drugs, depending on the dose, it may be possible to reduce the injection frequency from daily to once or twice monthly or even longer (6 months). In addition to improving patient comfort, less frequent injections of drugs in the form of depot formulations smoothes out the plasma concentration-time profile by eliminating the hills and valleys. Such smoothing out of plasma profiles has the potential to not only boost the therapeutic benefit in most cases, but also to reduce any unwanted events, such as immunogenicity.

Microparticles, implants and gels are the most common forms of biodegradable polymeric devices used in practice for prolonging the release of drugs in the body. Microparticles are suspended in an aqueous media right before injection and one can load as much as 40% solids in suspensions. Implant/rod formulations are delivered to SC/IM tissue with the aid of special needles in the dry state without the need for an aqueous media. This feature of rods/implants allows for higher masses of formulation, as well as drug content to be delivered. Further, in the rods/implants, the initial burst problems are minimized due to much smaller area in implants compared to the microparticles. Besides biodegradable systems, there are non-biodegradable implants and infusion pumps that can be worn outside the body. Non-biodegradable implants require a doctor's visit not only for implanting the device into the SC/IM tissue but also to remove them after the drug release period.

Injectable compositions containing microparticle preparations are particularly susceptible to problems. Microparticle suspensions may contain as much as 40% solids as compared with 0.5-5% solids in other types of injectable suspensions. Further, microparticles used in injectable depot products, range in size up to about 250 μm (average, 60-100 nm), as compared with a particle size of less than 5 μm recommended for IM or SC administration. The higher concentrations of solids, as well as the larger solid particle size require larger size of needle (around 18-21 gauge) for injection. Overall, despite the infrequent uses of larger and uncomfortable needles, patients still prefer less frequently administered dosage forms over everyday drug injections with a smaller needle.

Biodegradable polyesters of poly(lactic acid) (PLA) and copolymers of lactide and glycolide referred to as poly (lactide-co-glycolide) (PLGA) are the most common polymers used in biodegradable dosage forms. PLA is hydrophobic molecule and PLGA degrades faster than PLA because of the presence of more hydrophilic glycolide groups. These biocompatible polymers undergo random, non-enzymatic, hydrolytic cleavage of the ester linkages to form lactic acid and glycolic acid, which are normal metabolic compounds in the body. Resorbable sutures, clips and implants are the earliest applications of these polymers. Southern Research Institute developed the first synthetic, resorbable suture (Dexon®) in 1970. The first patent describing the use of PLGA polymers in a sustained release dosage form appeared in 1973 (U.S. Pat. No. 3,773,919).

Today, PLGA polymers are commercially available from multiple suppliers; Alkermes (Medisorb polymers), Absorbable Polymers International [formerly Birmingham Polymers (a Division of Durect)], Purac and Boehringer Ingelheim. Besides PLGA and PLA, natural cellulosic polymers such as starch, starch derivatives, dextran and non-PLGA synthetic polymers are also being explored as biodegradable polymers in such systems.

Therapeutic Uses

According to the principles of the present invention the peptides of the invention are useful in indications were insufficient blood-supply occurs, adequate blood vessels' growth and circulation is not properly restored, and there is a risk for tissue death due to insufficient blood flow or in cases of endothelia dysfunction. Typically, these conditions are for example peripheral vascular disease, myocardial ischemia, tissue graft diseases, coronary artery disease, stroke, and delayed wound healing (for example in ulcer lesions), pulmonary disease including acute lung injury (ALI), acute respiratory distress syndrome (ARDS), and ventilation induced ling injury (VILI), eye diseases including age-related macular disease (AMD) and pathological condition related to severe infection such as for example sepsis The peptides of the present invention are also useful for the treatment of diabetes and additional disease states which involve damage to pancreatic beta cells, or require the regeneration of these cells. Pancreatic islet vasculature has been shown to be a key determinant of the regenerative capacity of pancreatic beta cells. Among others, Brissova et al. (Diabetes 55:2974-2985, 2006) demonstrate that angiogenic factors and their receptors are differentially expressed in the adult pancreas, and reduced VEGF-A expression by pancreatic beta cells results in abnormal islet vascularization and a pre-diabetic phenotype, leading to a reduced insulin output into the vascular system. Angiogenic factors like VEGF are major regulators of pancreatic islet vascularization and function, and are furthermore required for revascularization of transplanted pancreatic islets. Thus, the peptides of this invention can be utilized for the treatment of diabetes in general, or for pancreatic islet transplantation in particular.

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

EXAMPLES

The following examples demonstrate the activity of the peptides of the present invention in stimulation of angiogenesis ex-vivo and in-vivo.

Example 1: Peptide Synthesis

The peptides were synthesized by conventional solid phase synthesis methods, using either tBoc or Fmoc chemistry.

Example 2: Aortic Ring Assay Ex-Vivo

Thoracic aortas were dissected from 7- to 8-week-old male SABRA mice. The aortas were immediately transferred to Petri dishes containing BIO-MPM-1. The adventitia and small vessels around the aorta were carefully removed under a dissecting microscope, and transverse cuts of 0.75 mm were made. The resulting aortic rings were extensively rinsed and incubated overnight in BIO-MPM-1 containing penicillin-streptomycin. Subsequently, the rings were embedded in 50 μl collagen mix (7 parts collagen, 1 part 10× Eagle minimal essential medium, MEM, and 2 parts 0.15 M sodium bicarbonate) in 96-well plates (Nunc, Rochester, N.Y.). Solidification of the collagen solution was achieved by raising the pH to neutral and the temperature to 37° C. 150 μl BIO-MPM-1 containing penicillin-streptomycin and the tested factors or peptides) was added to the embedded rings, and the plates were incubated at 37° C. in a humidified 10% CO2 atmosphere. Medium containing factors and/or peptides was refreshed at days 4 and 8. After two weeks, the rings were fixed with 4% formaldehyde for 24 hours, followed by staining with crystal violet (0.02%) dissolved in ethanol and extensive washing to remove excessive stain. The effect of factors and peptides was examined in 4 wells (4 rings of mouse aortic rings) per assay. Micrographs of representative rings were taken using a digital camera (Nikon, Tokyo, Japan). Morphometric analysis of sprouting was performed manually using Image-Pro 4.5 software (Media Cybernetics, Silver Spring, Md.) according to Nissanov et al. (Lab Invest. 1995; 73:734-739). Nonstained rings were subjected to paraffin sections and hematoxylin and eosin (H&E) staining.

Figure 1B:
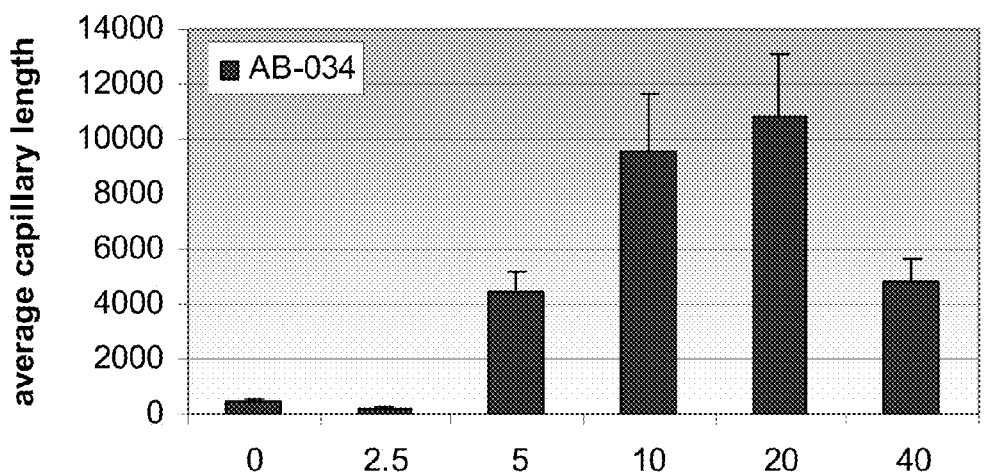
Figure 1C:
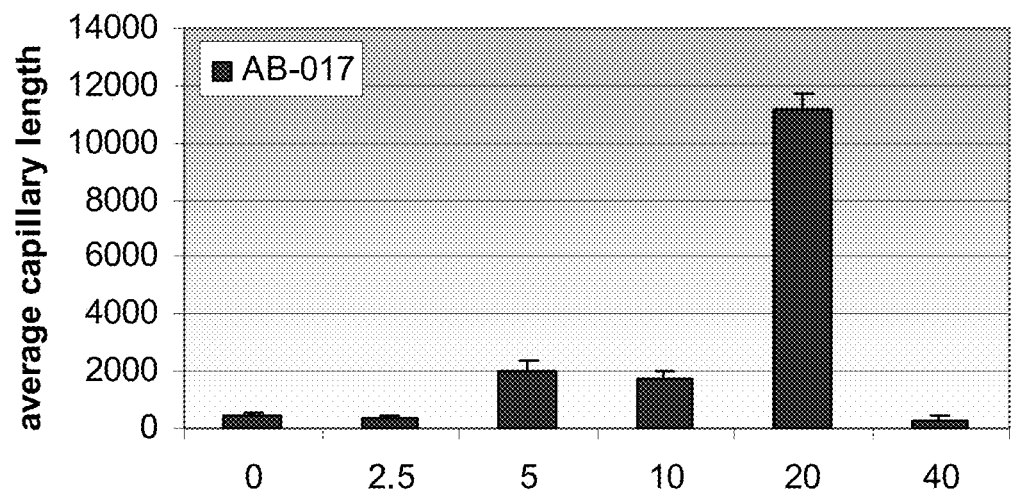
Figure 2A:
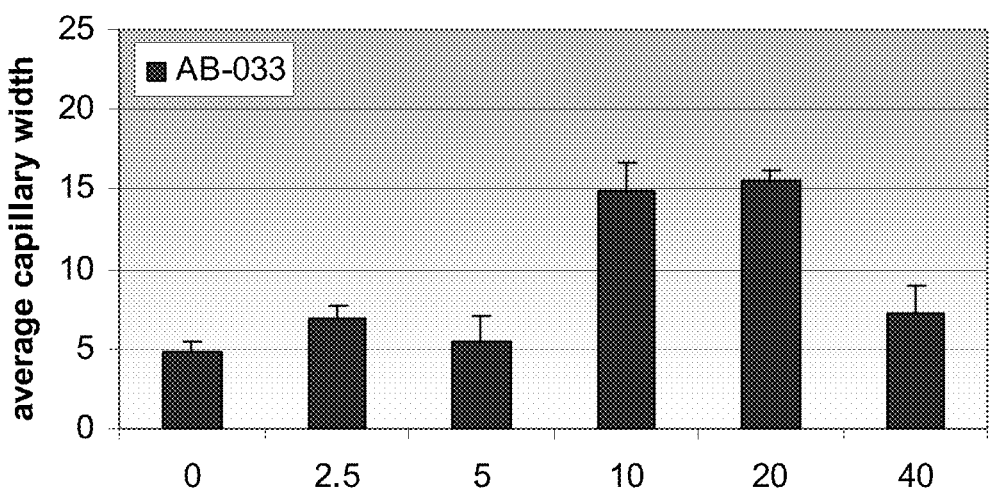
FIGS. 2A-C show an induction of capillary formation in aortic ring assay by the peptides of SEQ ID NOs: 13 (FIG. 1A), 14 (FIG. 1B), and 12 (FIG. 1C), as determined by aortic ring capillary width.
Figure 2B:
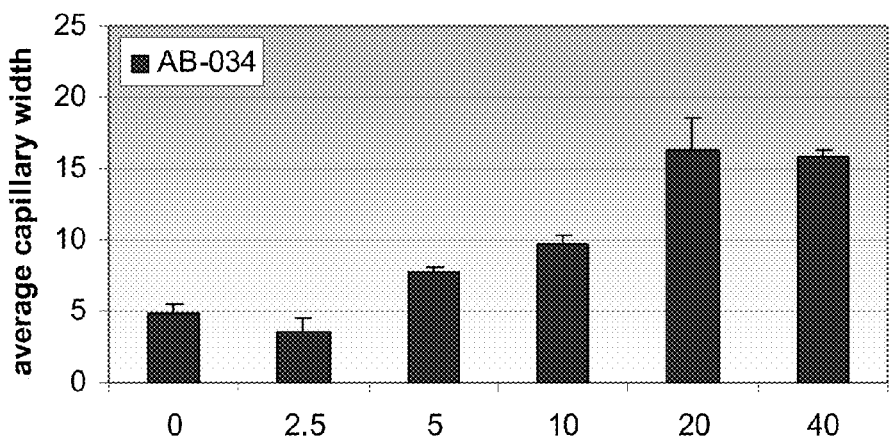
Figure 2C:
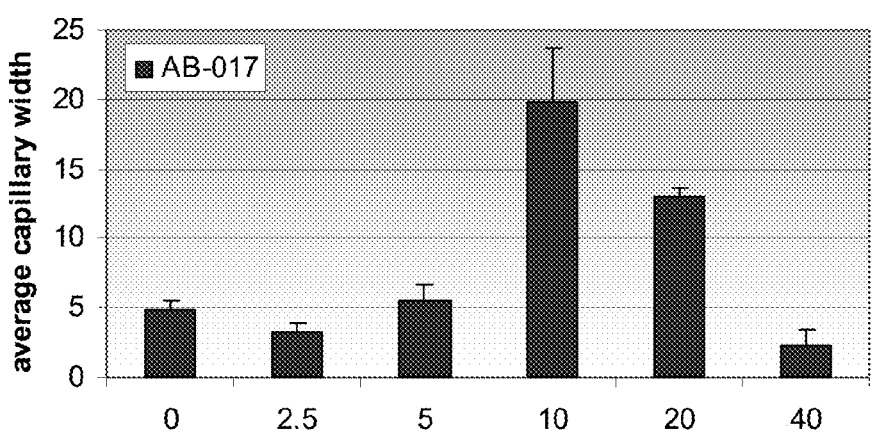

Table 2 summarizes the results of several compounds tested in several aortic ring assays. As demonstrated also in FIGS. 1A-1C and FIGS. 2A-2C, peptides AB-017 (SEQ ID NO: 12), AB-033 (SEQ ID NO: 13) and AB-034 (SEQ ID NO: 14) induce massive capillary formation in this assay. FIGS. 1A-1C represents aortic ring capillary length and FIGS. 2A-2C aortic ring capillary width. In the table: K-Flu is a Lysine residue coupled with a fluorescein moiety, 4BrPhe is 4-bromo-Phenylalanine, Dod is Dodecanoyl, Dec designates Decanoyl, Oct is Octanoyl, and Hex is Hexanoyl.

principle of the test is based on changes in perfusion rate, clinical signs and histological parameters (necrosis) following administration of the test compounds.

The mouse is the chosen species for the study, and historically has been used for the hind limb ischemia models, in the assessment and evaluation of potential pro-angiogenesis properties of tested compound. The mouse hind limb ischemia model is an initial step providing early information about efficacy of this strategy.

Each tested group included 4-7 mice per group. Intraperitoneal (i.p) injection is the preferred route of administration of the test items in this model and DMSO/PEG is used as vehicle to prepare the test item solution.

Tested peptides were dissolved in 100% DMSO. Thereafter Polyethylene glycol (PEG) 400 is added to the solution. Sterile water was used to dilute to a final concentration of 0.5% DMSO/10% PEG 400/$H_2O$ to result 2 mg/ml. The solution is prepared and divided into marked aliquots and stored at −70° C.

Species/Strain: Mice/Balb/c male~8 weeks
Source: Harlan Laboratories, Israel
Initial Body weight: Approximately 25 g at study initiation. The minimum and maximum weights of the group are within a range of ±20% of group mean weight.
Animals handling is performed according to guidelines of the National Institute of Health (NIH) and the Association for Assessment and Accreditation of Laboratory Animal Care (AAALAC).
Animals were housed under standard laboratory conditions, air conditioned and filtered (HEPA F6/6) with adequate fresh

TABLE 2

| Peptide | Z | 1 | 2 | 3 | 4 | 5 | 6 | 7 | B | Capillary length 10 μM | 10 μM | 20 μM | SEQ ID NO: |
|---|---|---|---|---|---|---|---|---|---|---|---|---|---|
| 725-106 | Myr-Gly | Nle | Arg | Pro | Tyr | Asn | Ala | | $NH_2$ | 7,000 | | 4,600 | 2 |
| AB-018 | Myr-Gly | Nle | Arg | Pro | Tyr | Asn | | | $NH_2$ | 12,600 | | 10,200 | 24 |
| AB-017 | Myr-Gly | Nle | Arg | Pro | Tyr | | | | $NH_2$ | 15,300 | | 15,300 | 12 |
| AB-016 | Myr-Gly | | Arg | Pro | Tyr | | | | $NH_2$ | 8,700 | | 14,500 | 11 |
| AB-015 | Acetyl-Gly- | | Arg | Pro | Tyr | | | | $NH_2$ | 1,000 | | 1,700 | 25 |
| AB-014 | | | Arg | Pro | Tyr | | | | $NH_2$ | 2,500 | | 9,300 | |
| AB-013 | Myr-Gly | Nle | Arg | Pro | Tyr | Asn | DAla | | $NH_2$ | 8700 | | 900 | 26 |
| AB-011 | Myr-Gly | Nle | Arg | Pro | Tyr | Asn | Ala | K-Flu | $NH_2$ | 2500 | | 5000 | 27 |
| vehicle | | | | | | | | | | 1,700 | | 1,700 | |
| AB-017 | Myr-Gly | Nle | Arg | Pro | Tyr | | | | | 1,720 | 3,100 | 11,200 | 12 |
| AB-033 | Myr-Gly | Nle | Arg | Pro | 35dIY | | | | | 3,570 | | 3,800 | 13 |
| AB-034 | Myr-Gly | Nle | hArg | Pro | Tyr | | | | | 9,570 | 9,700 | 10,780 | 14 |
| AB-031 | Myr-Gly | Nle | Arg | Pro | 4BrPhe | | | | | | 1,840 | | 28 |
| vehicle | | | | | | | | | | 490 | 0 | 490 | |
| AB-017 | Myr-Gly | Nle | Arg | Pro | Tyr | | | | | 3,100 | 3,770 | | 12 |
| AB-020 | Dod-Gly | Nle | Arg | Pro | Tyr | | | | | 1,900 | 5,600 | 2,700 | 29 |
| AB-021 | Dec-Gly | Nle | Arg | Pro | Tyr | | | | | 590 | 3,940 | 3,200 | 30 |
| AB-022 | Oct-Gly | Nle | Arg | Pro | Tyr | | | | | 380 | 2,170 | 1,700 | 31 |
| AB-023 | Hex-Gly | Nle | Arg | Pro | Tyr | | | | | 430 | 1,700 | 320 | 32 |
| vehicle | | | | | | | | | | 0.0 | 1,370 | 0.0 | |
| AB-017 | Myr-Gly | Nle | Arg | Pro | Tyr | | | | | 1,720 | | 11,200 | 12 |
| AB-033 | Myr-Gly | Nle | Arg | Pro | 35dIY | | | | | 3,570 | | 3,800 | 1013 |
| AB-034 | Myr-Gly | Nle | hArg | Pro | Tyr | | | | | 9,570 | | 10,780 | 14 |
| vehicle | | | | | | | | | | 490 | | 490 | |

Example 3: Efficacy Study—Mouse Hind Limb Ischemia/Angiogenesis Model

The object of this study was to determine whether administration of the test items, peptides AB-017 (SEQ ID NO: 12) and 725-106 (positive control, SEQ ID NO: 2) can enhance angiogenesis, subsequently inducing clinical and motor function improvement in a hind limb ischemia model. The air supply (31 air changes/hour). Animals were kept in a climate controlled environment. Temperatures range is between 20-24° C. and RH is between 30-70% with 12 hours light and 12 hours dark cycle. Animals were housed in polyethylene cages (7/cage) measuring 35×30×15 cm, with stainless steel top grill facilitating pelleted food and drinking water in plastic bottle; bedding: steam sterilized clean paddy husk. Bedding material is changed along with the cage at least twice a week.

Diet: Animals are fed ad libitum a commercial rodent diet (Teklad Certified Global 18%
Protein Diet cat #: 106S8216). Animals have free access to drinking water obtained from the municipality supply.
Surgical Procedure:
Anesthesia: Isoflurane 1.5-3% in a mixture of $O_2/N_2O$, under spontaneous respiration. All four limbs of the animal were taped down in order to facilitate the animal for surgery. Both hind legs of the animals are shaved and disinfected. On the operated leg, the right leg in all animals, an incision was made from the inguinal area to the proximity of the knee. The femoral vein/artery/nerve were exposed. The artery is dissected free from the vein, nerve and surrounding fascia. Distal to its bifurcation with the profound femoral artery, using 6-0 silk suture the artery is ligated twice, and thereafter transected between these two points (see prox-A-group model appendix I). The surgical wound is closed with 6-0 silk and the mouse is returned to its cage. The left leg is untreated control in all animals.
Exclusion criteria: Only mice, whose mean flux measurement post surgery is ≤10% and ≤50% of the pre surgical measurement, are incorporated into the study. Mice whose mean flux measurement post surgery out of this range were excluded from the study.

$$\text{Calculation: Mean Flux} = \frac{(\text{Pre Treated} - 0.5)/(\text{Pre Control} - 0.5)}{(\text{Post Treated} - 0.5)/(\text{Post Control} - 0.5)}$$

Drug administration: All animals were dosed by IP administration at a dose volume of 10 ml/kg.

TABLE 3

Treatment scheme:

| Group No. | Treatment | Dose Level mg/kg | Frequency of Dosing |
|---|---|---|---|
| 1M | Vehicle | NA | Twice weekly for 4 weeks (First application on the day following surgery) |
| 2M | AB-017 | 20 | |
| 3M | 725-106 Positive control | 20 | |

Figure 3:
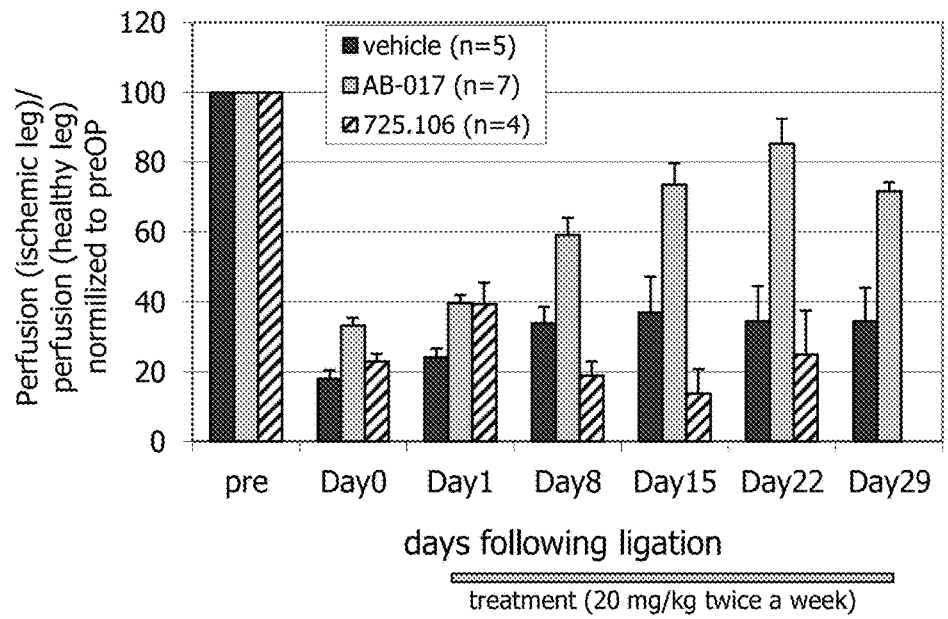
FIG. 3 shows the effects of compound of SEQ ID NO: 9 vs. compound of SEQ ID NO: 1 on perfusion (LDI) in ischemic leg model in mice.

Tests and Evaluation:
Body weight: Body weights were measured prior to surgery, prior to each dosing, and prior to necropsy.
Blood flow measurement: Using a Laser Doppler apparatus (Perimed PeriScan PIM II System, Technical manual available at test facility) Blood flow was measured (operated leg & control leg) while the legs are in their natural resting position at the following time points: Before surgery (after shaving) & Post surgery (Day 0); Day 1; Day 8; Day 15; Day 22; and Day 29. Each time point for each mouse consists of three measurements.
Blood flow was measured, additionally, in first 10 animals at Pre before shaving.
Macroscopic evaluation of ischemic severity: Two weeks after the operation and at study end, the ischemic limb was macroscopically evaluated by using a 5 point graded morphological scale for necrotic area; Grade 0: No change; Grade 1: Toe necrosis (limited to); Grade 2: Foot necrosis (extending to a dorsum pedis); Grade 3: Knee necrosis (extending to knee); Grade 4: Total necrosis (total hind-limb loss), according to Tokai. J. et al. (Exp. Clin. Med., 31, 3, pp. 128-132, 2006).
Assessment of limb motor function damage: Two weeks after the operation and at study end assessment of limb motor function was performed using the following 4 point scale: Grade 0: Flexing the toes to resist gentle traction of the tail; Grade 1: plantar flexion; Grade 2: No dragging but no plantar flexion; Grade 3: Dragging of foot (Rutherford et al., J. Vascular Surgery; 1997, 26, 517-538). Termination muscle weight & tissue fixation: At study termination Day 29, animals are sacrificed. The following muscles were dissected free of the leg, weighted and fixed in formalin until retrieved by the Sponsor: Anterior Tibial, Gastrocnemius, and Soleus.
Results
Data compilation: Data was summarized in a graphical form showing perfusion of the operated leg for 4 weeks (FIG. 3, Numerical results are given as means and standard errors), and in a tabular form (Table 4) showing for each group the number of animals, scores of leg function and scores of ischemic condition of the leg at day 15. Only animals whose leg perfusion was decreased >50% post operation were included in this analysis.
Ischemic Score
4: necrosis extending to a thigh (total hind-limb loss)
3: necrosis extending to a crus (knee loss)
2: necrosis extending to a dorsum pedis (foot loss)
1: necrosis limiting to toes (toes loss)
0: absence of necrosis
Function Score
3: dragging of foot
2: no dragging but no plantar flexion
1: plantar flexion
0: flexing the toes to resist gentle traction of the tail (Rutherford et al., 1997).
FIG. 3 and Table 4 summarize the results of treatments with compounds AB-017 (SEQ ID NO: 12), and 725-106 (positive control, SEQ ID NO: 2) as compared to vehicle control in the hind limb ischemia model in vivo. As can be seen, in all parameters of perfusion (FIG. 3), leg function and leg necrosis (Table 4) treatment with AB-017 leads to a significant improvement of the ischemic leg as compared to both the vehicle control and the longer peptide 725-106.

TABLE 4

| Treatment | Mouse # | Hind limb ischemia evaluation at day 15 | Functional evaluation at day 15 |
|---|---|---|---|
| Vehicle | 39 | 2.5 | 3.0 |
| | 43 | 1.0 | 1.0 |
| | 19 | 3.0 | NA |
| | 30 | 2.3 | 3.0 |
| | 82 | 0.0 | 0.0 |
| | Average | 1.8 | |
| AB-107 | 46 | 2.0 | 3.0 |
| | 38 | 2.0 | 3.0 |
| | 42 | 0.0 | 2.0 |
| | 78 | 0.0 | 0.0 |
| | 15 | 1.0 | 0.0 |
| | 28 | 0.0 | 0.0 |
| | 66 | 0.0 | 0.0 |
| | Average | 0.7 | |
| 106 (Positive control) | 44 | 2.0 | 3.0 |
| | 40 | 3.0 | NA |
| | 33 | 2.5 | 3.0 |
| | 16 | 2.0 | 3.0 |
| | Average | 2.4 | |

Example 4: In Vivo Efficacy—Angiogenesis Model in Mice

The aim of this study was to test the pro-angiogenic activity of the peptides in the mouse myocardial infarction model and to determine whether administration of peptides can induce blood vessel growth in this model and whether, as a result, improvement in clinical function of the ischemic heart can be demonstrated. The principle of the test is based on changes in perfusion rate, clinical signs and histological parameters following administration of the test peptides. Study end points include measurement of ECG and measurement of myocardial damage.

The mouse is the chosen species for the study, and historically has been used for the myocardial infarction studies, in the assessment and evaluation of potential pro-angiogenesis properties of tested compound. The mice myocardial infarction ischemia model is usually an initial step providing early information about efficacy of this strategy.

A total of 30 mice were utilized. Each tested group included 10 mice. Intraperitoneal (i.p) injection is the preferred route of administration of the tested compounds in this model and DMSO/PEG is used as vehicle to prepare the test item solution.

Materials and Methods

Tested peptides were dissolved in 100% DMSO. Thereafter Polyethylene glycol (PEG) 400 is added to the solution. Sterile water is use to dilute to a final concentration of 0.5% DMSO/10% PEG 400/H2O to result 2 mg/ml. The solution is prepared and divided into marked aliquots and stored at −70° C.

Species/Strain: Mice/F1 hybrid CB6F1 (C57BL/6J× BALBc)
Gender/Number/Age: Male/30 (3 groups)/8 weeks
Source: Harlan Laboratories, Israel
Body weight: Approximately 25 g at study initiation. The minimum and maximum weights of the group will not exceed ±20% of group mean weight.
Acclimation period: Minimum 5 days.
Identification: By mice accession number, ear notching and cage cards.

Animals handling was according to the National Institute of Health (NIH) and the Association for Assessment and Accreditation of Laboratory Animal Care (AAALAC).

Animals were housed in polyethylene cages (4/cage) measuring 35×30×15 cm, with stainless steel top grill having facilities for pelleted food and drinking water in glass bottle; Animals are housed under standard laboratory conditions, air conditioned and filtered (HEPA F6/6) with adequate fresh air supply (31 air changes/hour). Animals were kept in a climate controlled environment. Temperatures range is between 20-24° C. and RH is between 30-70% with 12 hours light and 12 hours dark cycle. Steam sterilized clean paddy husk (Harlan, Sani-chip cat#:2018SC+F) are used and bedding material is changed along with the cage at least twice a week. Animals were fed ad libitum "free-feeding" a commercial rodent diet (Teklad Certified Global 18% Protein Diet cat#: 106S8216). Animals had free access to tap drinking water. Reasonably expected contaminants in food and water supplies should not have the potential to influence the outcomes of this test. Animals were randomized using a computer generated randomization program "Research Randomizer" and divided into 3 groups of 10 animals.

Experimental Design and Conditions

The animal was anesthetized with Pentobarbital sodium (70 mg/kg). The landmark for the incision is the left armpit. Lidocaine, 0.1 ml of 0.1% solution, was injected subcutaneously. An oblique 8-mm incision was made 2 mm away from the left sternal border toward the left armpit (1-2 mm below it). The operator tried to visualize the superficial thoracic vein that runs under the skin at the lateral corner of the incision. Both layers of thoracic muscles were cut, taking caution to avoid the vein; through the thin and semitransparent chest wall, the ribs and inflating lung are visible. The $4^{th}$ intercostal space represents the area between those ribs where the lowest part of the lung is observed. The chest cavity was then opened taking caution not to damage the lung. The chest retractor is inserted and opened gently to spread the wound 8-10 mm in width. The heart partially covered by the lung was then visualized. The pericardium was gently picked up with curved and straight forceps, pulled apart, and placed behind the arms of the retractor. This maneuver pushes the lung up slightly, mobilizing it and providing better exposure of the heart. The left anterior descending coronary artery (LAD) was then visualized as a pulsating bright red spike, running in the midst of the heart wall from underneath of the left atrium toward the apex. If the LAD artery cannot be visualized, the left atrium can be lifted so that the origin of the LAD artery from the aorta is located. The LAD artery was ligated 1-2 mm below the tip of the left auricle in its normal position, which induces roughly 40-50% ischemia of the left ventricular (LV). Once the site of ligation has been determined, the curved forceps were used to gently press on the artery a little below the subsequent ligation (this enhance the view of the artery and stabilize the heart). Occlusion was confirmed by the change of color (becoming pale) of the anterior wall of the LV. The retractor was removed, and the lungs were reinflated by shutting off the ventilator outflow. The chest cavity was closed by bringing together the 4th and the 5th ribs with one or two 6-0 nylon sutures (with pressure applied to the chest wall to reduce the volume of free air). The muscles and skin were closed layer by layer with 6-0 absorbable and nylon sutures, respectively. The duration of the whole procedure took about 12-15 min.

Drug Administration:

First dosing was done by IP administration of 20 mg/kg of the tested compound in 10 ml/kg solution, approximately 45-120 min after induction of myocardial infarction only on recovered animals, spontaneous breathing animals and thereafter twice weekly.

TABLE 5

Groups allocation

| Group # and No. animals | Treatment | Dose Level µg/kg |
|---|---|---|
| 1M (n = 10) | Vehicle | N/A |
| 2M (n = 10) | AB-017 (SEQ ID NO: 12) | 20 mg/kg |
| 3M (n = 10) | AB-034 (SEQ ID NO: 14) | 20 mg/kg |

Tests and Evaluation:

Body weight: Body weight was measured on study day prior to dosing at each dosing day.

ECG measurements: The inductions of myocardial infarction are confirmed by an ECG ST segment elevation after LAD artery occlusion (before and immediately after occlusion). Thereafter, ECG measurements are made once a week after cardiac infarction by a BIOPAC system.

LDH measurement: Blood (150 µl) is collected from each mouse at the conclusion of 24 hours and is stored for 1 to 2 hours at room temperature. Serum is obtained by centrifugation at 2,000 rpm for 10 min and stored at −70° C. LDH was measured with a standard Elisa Kit.

Termination: At study termination 4 weeks after operation the animals were sacrificed and gross pathology was performed. The hearts were excised and cannulated through the ascending aorta with a 23-gauge needle for sequential perfusion with 2 to 3 mL 37° C. 0.9% sodium chloride and with 3 to 4 mL 37° C. 1.0% TTC in phosphate buffer (pH 7.4). The hearts were then perfused with 2 to 3 ml of 10%/o Phthalo Blue (Heubach Ltd) to delineate nonischemic myocardium. Hearts were weighed and photographed from both sides with a digital camera. Image J was used to digitally planimeter the borders of the entire heart, the nonischemic area, and the infracted area on both sides of each slice. The sizes of the nonischemic area and ischemic area (area at risk) were calculated as size in mm$^2$ or as percentages of the total area multiplied by the total weight of the heart.

Example 5: Whole-Mount Immune Staining of Aortic Rings

Rings embedded and grown in collagen (as described in "Aortic ring assay") were fixed with 1% paraformaldehyde in PBS for 30 minutes at room temperature and left overnight in PBS. Blocking and permeabilization of the fixed rings was achieved by incubation with PBS containing 1% BSA and 0.01% Triton-X 100 for 8 hours at 4° C. The rings were incubated with FITC-conjugated anti alpha smooth muscle actin antibody (ab8211, diluted 1:200; Abcam, Cambridge, England) in PBS containing 1% BSA for 8 hours. After removal of excess unbound antibody by several washes with PBS during the next 8 to 10 hours, the samples were visualized using a fluorescent microscope (Axiovert 200M; Zeiss).

Example 6: Corneal Pocket In-Vivo Assay

The corneal pocket assay tests blood vessel formation from the limbus in a mouse eye towards a pellet containing the tested material/s, inserted to the cornea of the eye.

Angiogenic responses were examined as described by Kenyon et al. (Invest Ophthalmol Vis Sci. 1996; 37:1625-1632). Briefly, pellets were prepared by dissolving sucralfate (500 mg/mL) in 20 mM sodium citrate, 1 mM EDTA, and 9% sucrose solution, and 20 μl of this solution was added to 5 mg of the tested peptide, or 40 g of FGF, VEGF or CSF. Single pellets contained approximately 1:450 of these amounts. Following addition of 20 μL Hydron polymer in ethanol (120 mg/mL), the mixtures were applied to a 15×15-mm$^2$ piece of synthetic mesh (Sefar America, Kansas City, Mo.) and coated by Hydron. The pellets were allowed to air dry, and fibers of the mesh were pulled apart. Corneal micropockets were created in both eyes of anesthetized C57BL/6 mice (8-10 weeks old). Incisions were made after local administration of lidocaine, using a Von-Graefe cataract knife. Pellets (0.2×0.2×0.3 mm) were impregnated into the corneal micropockets at a distance of 1 to 2 mm from the vascularized limbus. In case of peptide and protein combinations, 2 pellets were inserted to the same incision. Polymyxin-B-neomycin-bacitracin (Bamyxin) ophthalmic ointment was applied to the eyes to prevent infection. Responses were recorded and photographed after 8 days using stereoscopy. Vessel development was monitored twice weekly until full microscope, and transverse cuts of 0.5 mm were made. The resulting aortic vessel regression occurred. Each peptide and factor tested in this assay was examined in 4 animals (4-6 eyes).

Example 6: Synergistic Effect

Figure 4:
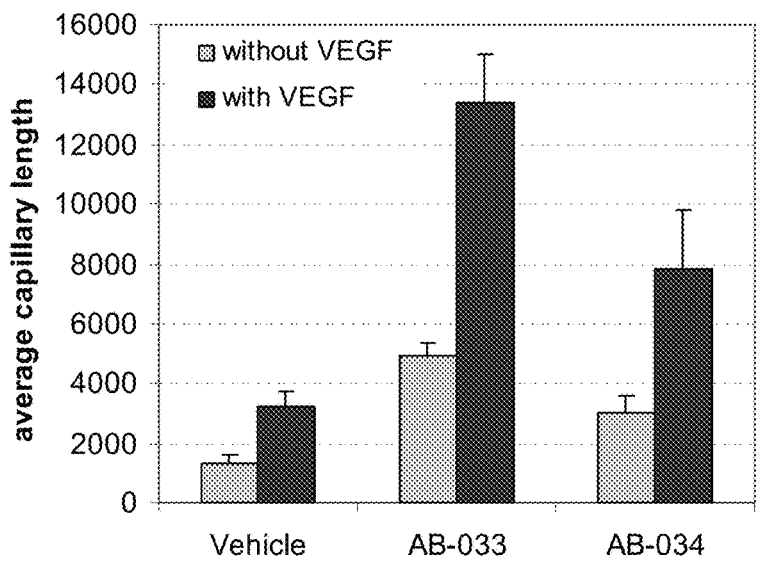
FIG. 4 represents synergistic effect of peptides of SEQ ID NOs: 13 and 14 with VEGF in aortic ring assay.

The aortic ring assay was repeated in the presence of 10 μM concentration of peptides AB-033 (SEQ ID NO: 13) and AB-034 (SEQ ID NO: 14) together with the pro-angiogenetic protein VEGF. The results shown in Table 6 and in FIG. 4 demonstrate a synergistic effect of treatment with the peptides together with VEGF.

TABLE 6

| Treatment | Average capillary length | SE | Fold vs vehicle |
|---|---|---|---|
| Vehicle | 1369 | 244 | 1.0 |
| VEGF | 3221 | 508 | 2.4 |
| AB-033 | 4941 | 392 | 3.6 |
| AB-033 + VEGF | 13402 | 1591 | 9.8 |
| AB-034 | 3062 | 558 | 2.2 |
| AB-034 + VEGF | 7818 | 1995 | 5.7 |

Example 7: Additional Peptides

Table 7 lists additional peptides which are peptide analogs of the peptides disclosed above. These peptides are being synthesized and tested for stimulation of angiogenesis.

TABLE 7

| Modification | Peptide | Z | 1 | 2 | 3 | 4 | B | SEQ ID NO: |
|---|---|---|---|---|---|---|---|---|
| Arg$^2$ | AB-017 | Myr-Gly | Nle | Arg | Pro | Tyr | NH$_2$ | 12 |
| | AB-066 | Myr-Gly | Nle | X | Pro | Tyr | NH$_2$ | 33 |
| | AB-067 | Myr-Gly | Nle | Cit | Pro | Tyr | NH$_2$ | 34 |
| | AB-0 | Myr-Gly | Nle | Lys | Pro | Tyr | NH$_2$ | 35 |
| | AB-0 | Myr-Gly | Nle | Gln | Pro | Tyr | NH$_2$ | 36 |
| spacer | AB-0 | Myr-βAla | Nle | hArg | Pro | Tyr | NH$_2$ | 37 |
| | AB-0 | Myr-βAla | Nle | Arg | Pro | Tyr | NH$_2$ | 38 |
| Z | AB-0 | Cho-Gly | Nle | hArg | Pro | Tyr | OH | 39 |
| | AB-0 | Cho-Gly | Nle | Arg | Pro | Tyr | OH | 40 |
| B | AB-0 | Myr-Gly | Nle | hArg | Pro | Tyr | OR | 41 |
| | AB-0 | Myr-Gly | Nle | Arg | Pro | Tyr | OR | 42 |
| N-methylation | AB-0 | Myr-Gly | NMeNle | Arg | Pro | Tyr | NH$_2$ | 43 |
| | AB-0 | Myr-Gly | Nle | NMeArg | Pro | Tyr | NH$_2$ | 44 |
| | AB-061 | Myr-Gly | NMeNle | hArg | Pro | Tyr | NH$_2$ | 45 |
| Pro$^3$ | AB-068 | Myr-Gly | Nle | hArg | Z1 | Tyr | NH$_2$ | 46 |
| | AB-0 | Myr-Gly | Nle | Arg | Z1 | Tyr | NH$_2$ | 47 |
| | AB-064 | Myr-Gly | Nle | hArg | 4HyP | Tyr | NH$_2$ | 48 |
| | AB-0 | Myr-Gly | Nle | hArg | 3HyP | Tyr | NH$_2$ | 49 |
| | AB-0 | Myr-Gly | Nle | Arg | 4HyP | Tyr | NH$_2$ | 50 |
| | AB-0 | Myr-Gly | Nle | Arg | 3HyP | Tyr | NH$_2$ | 51 |
| | AB-065 | Myr-Gly | Nle | hArg | Z2 | Tyr | NH$_2$ | 52 |
| | AB-0 | Myr-Gly | Nle | Arg | Z2 | Tyr | NH$_2$ | 53 |

TABLE 7-continued

| Modification | Peptide | Z | 1 | 2 | 3 | 4 | B | SEQ ID NO: |
|---|---|---|---|---|---|---|---|---|
| Tyr[4] | AB-032 | Myr-Gly | Nle | Arg | Pro | 4NF | $NH_2$ | 54 |
|  | AB-0 | Myr-Gly | Nle | hArg | Pro | 4NF | $NH_2$ | 55 |
|  | AB-070 | Myr-Gly | Nle | hArg | Pro | 35dIY | $NH_2$ | 56 |

Myr is a myristoyl, Cho is a cholesteryl, X is an 2-amino-3-guanidinopropionic acid, hArg is homoarginine, Cit is a citruline, R is a lower alkyl group, Z1 is (S)-thiazolidine-2-carboxylic acid, Z2 is (2S,3aS,7aS) Octahydro-1H-indole-2-carboxylic acid, NMeArg is N-methyl arginine, NMeNle is N-methyl Norleucine, 4HyP is (4-hydroxy)proline, 3HyP is (3-hydroxy)proline, 4NF is (4-$NH_2$) Phenylalanine, and 35dIY is (3,5-diiodo)tyrosine.

Example 8: Inhibition of Blood-Vessel Leakiness

The peptide of SEQ ID NO: 12 (Myr-Gly-Nle-Arg-Pro-Tyr-$NH_2$), or vehicle (10% PEG-400, 90% DDW), were injected i.p. to mice, in an amount of 20 or 40 mg/Kg. 5 min, 10 min, 1 hr or 4 hrs later, 0.2 ml per 25 g mouse (40 mg/Kg) of 5 mg/ml Evans-Blue solution in double distilled water (DDW) was injected i.p. The experiment was terminated after 30 min and skull was opened to view the brain surface ("Neurosurgery") and assess the amount of Evans-Blue leaking from blood vessels.

Principle of peripheral vessels staining: Evans-Blue; it is a poly-anionic compound having a M.W. of 960 Dalton, that binds tightly to albumin and being used to track vessel-permeability. In case of blood-vessel leakiness, the Evans-Blue-albumin complex escapes from the blood-stream into the surrounding interstitial fluid with the result of blue coloring of the extremities and the bluish appearance at the brain surface.

In a specific experiment, 40 mg/kg of peptide of SEQ ID NO: 12 or vehicle were injected, each to 2 mice, i.p. 5 min before color injection. Evans-blue, at 40 mg/kg was then injected i.p. and 30 min later "Neurosurgery" was performed and the escape of the color from the blood stream was monitored as manifested by the bluish appearance of the brain surrounding tissue. The results clearly demonstrate that while Evans-Blue was leaking from blood-vessels of control mice (Vehicle-injected), as evident by the brain's bluish color, no color was leaking from vessels of animals pre-treated with peptide SEQ ID NO: 12.

In an additional experiment, 20 mg/kg of peptide of SEQ ID NO: 12 or vehicle (10%/PEG-400, 90% DDW) were injected i.p. into 2 mice, 10 min before color injection (Evans-blue, 40 mg/kg i.p. for 30 minutes. The results clearly demonstrate that while Evans-Blue was leaking from blood-vessels of control mice (Vehicle-injected), as evident by the brain's bluish color and the bluish color of the paws, no color was leaking from vessels of animals pre-treated with peptide SEQ ID NO: 12, neither at the brain, nor at the periphery.

In another experiment, 40 mg/kg of peptide SEQ ID NO: 12 were injected to mice, i.p. 1 or 4 hours before color injection (Evans-blue, 40 mg/kg i.p. for 30 minutes). Control mice received i.p. injection of vehicle (10%/PEG-4 i.p. 00, 90% DDW) 1 hour before color injection. The results clearly demonstrate that while Evans-Blue was leaking from blood-vessels of control mice (Vehicle-injected), as evident by the brain's bluish color, no color was leaking from vessels of animals pre-treated with peptide SEQ ID NO: 12, 1 hr before Evans-Blue injection, while the injection of the peptide 4 hrs before Evans-Blue gave only a partial protection. i.e. the appearance of faint-bluish color.

Example 9: In-Vivo Septic Shock Model

The polymicrobial septic mouse model of severe sepsis (Belikoff et al. The Journal of Immunology, 2011, 186: 2444-2453), was induced in wild-type (WT) C57BL mice using cecum ligation and puncture (CLP) approach. In summary, mice were anesthetized, a 1.5-cm, longitudinal incision in the lower right quadrant of the abdomen was performed and the cecum was exposed. The distal two third of the cecum was ligated with 4-0 silk suture and punctured doubly with an 18-gauge needle. The cecum was then replaced into the peritoneal cavity and the incision was closed with surgical staples. After that, the mice were resuscitated with sterile saline injected subcutaneously and allowed free access to food and water after awaking.

Following this procedure, mice were then injected s.c. once a day, for 5 days, with either vehicle or with 20 mg/Kg of GPS-725.017 (SEQ ID NO: 12).

Figure 5:
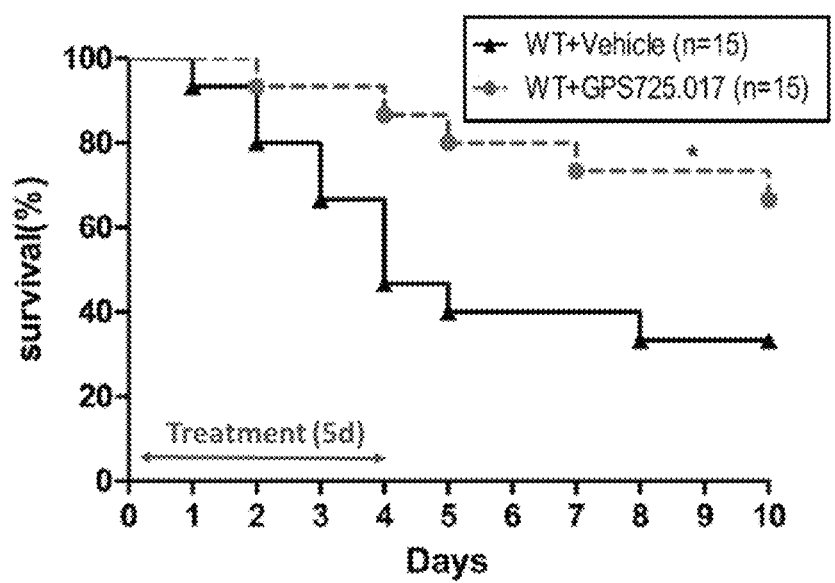
FIG. 5 depicts in-vivo results which demonstrate the ability of peptide SEQ ID NO: 12 (GPS-725.017) to rescue mice from death in a septic-shock model. C57BL mice (15 for each group) were injected s.c. once a day, for 5 days, with either vehicle or 20 mg/Kg of GPS-725.017 (SEQ ID NO: 12).

The results depicted in FIG. 5 demonstrate that the ability of peptide SEQ ID NO: 12 (denoted GPS-725.017 in the chart) to rescue mice from death in an established septic-shock in-vivo model.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A peptide consisting of 4-5 amino acids, the peptide having the sequence Nle-RPY, wherein Nle is norleucine, R is selected from the group consisting of an arginine residue, an homoarginine residue (hArg), an N-methyl arginine residue (NMeArg), a citruline residue, and a 2-amino-3-guanidinopropionic acid residue; P is selected from the group consisting of a proline residue, an hydroxyproline residue, and a thiazolidine-carboxylate residue, and Y is selected from the group consisting of: a tyrosine residue, a 3,5 diiodo tyrosine residue (35dITyr), a 3,5 diBromo tyrosine residue (35dBTyr), and an homotyrosine residue.

2. A peptide conjugate comprising a peptide according to claim 1 and a moiety capable of increasing permeability, wherein the peptide-conjugate is according to Formula I:

i. Z—X—R—P—Y—B     (Formula I)

wherein Z designates a moiety capable of increasing permeability covalently connected via a direct bond or via a linker; X designates Nle, R is selected from the group consisting of an arginine residue, an homoarginine residue (hArg), an N-methyl arginine residue (NMeArg), a citruline residue, and a 2-amino-3-guanidinopropionic acid residue; P is selected from the group consisting of a proline residue, an hydroxyproline residue, and a thiazolidine-carboxylate residue, and Y is selected from the group consisting of: a tyrosine residue, a 3,5 diiodo tyrosine residue (35dITyr), a 3,5 diBromo tyrosine residue (35dBTyr), and an homotyrosine residue, and B designates a terminal carboxy acid, amide, ester or alcohol group.

3. The peptide conjugate of claim 2 wherein Z designates Myristoyl-glycine (Myr-Gly), X is a norleucine (Nle) residue, R is an arginine residue or an homoarginine residue (hArg), P is a proline residue or 4-hydroxy-Proline residue (4HyP), Y is a tyrosine residue or a (3,5-diiodo)tyrosine (35dITyr) residue and B is terminal designates a terminal carboxy acid, amide, ester or alcohol group.

4. The peptide conjugate according to claim 2 comprising a peptide selected from the group consisting of:

```
Gly-Nle-Arg-Pro-Tyr-NH2;         (SEQ ID NO: 6)

Gly-Nle-Arg-Pro-35dITyr-NH2;     (SEQ ID NO: 7)

Gly-Nle-hArg-Pro-Tyr-NH2;        (SEQ ID NO: 8)

Gly-Nle-hArg-Pro-35dITyr-NH2;    (SEQ ID NO: 9)
and

Gly-Nle-hArg-4HyP-Tyr.           (SEQ ID NO: 10)
```

5. The peptide conjugate of claim 2 selected from the group consisting of:

```
Myr-Gly-Nle-Arg-Pro-Tyr-NH2;         (SEQ ID NO: 12)

Myr-Gly-Nle-Arg-Pro-35dITyr-NH2;     (SEQ ID NO: 13)

Myr-Gly-Nle-hArg-Pro-Tyr-NH2;        (SEQ ID NO: 14)

Myr-Gly-Nle-hArg-Pro-35dITyr-NH2,    (SEQ ID NO: 15)
and

Myr-Gly-Nle-hArg-4HyP-Tyr.           (SEQ ID NO: 16)
```

6. A pharmaceutical composition comprising as an active ingredient a peptide according to claim 1, and a pharmaceutically acceptable carrier.

7. A pharmaceutical composition comprising as an active ingredient a peptide conjugate according to claim 2 and a pharmaceutically acceptable carrier.

8. A method of prevention or treatment a condition in which insufficient blood-supply occurs, a condition which is associated with endothelia dysfunction, or a condition mediates through S1P receptor, comprising administering to a subject in need thereof a pharmaceutical composition according to claim 7.

9. The method of claim 8 wherein the condition is selected from the group consisting of: peripheral vascular disease, myocardial ischemia, tissue graft, coronary artery diseases, stroke, diabetes, pancreatic islet transplantation, and delayed wound healing, pulmonary disease, eye disease, bone loss and pathological condition related to severe infection.

10. The method according to claim 9 wherein the disease is selected from the group consisting of: acute lung injury (ALI), acute respiratory distress syndrome (ARDS), and ventilation induced ling injury (VILI); age-related macular disease (AMD); and sepsis.

11. A stent comprising at least one peptide conjugate according claim 2.

12. A method of prevention or treatment of myocardial infection or coronary artery disease, comprising administering to a subject in need thereof a stent according to claim 11.

13. The peptide of claim 1 wherein R is an arginine residue or an homoarginine residue (hArg), P is a proline residue or 4-hydroxy-Proline residue (4HyP), and Y is a tyrosine residue or a (3,5-diiodo)tyrosine (35dITyr) residue.

14. A peptide conjugate consisting of Myr-Gly-Nle-Arg-Pro-Tyr-NH2 (SEQ ID NO: 12).

* * * * *

SEQUENCE LISTING

<160> NUMBER OF SEQ ID NOS: 56

<210> SEQ ID NO 1
<211> LENGTH: 10
<212> TYPE: PRT
<213> ORGANISM: Artificial sequence

```
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE

<400> SEQUENCE: 1

Gly Met Arg Pro Tyr Asp Ala Asn Lys Arg
1               5                   10

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Nle

<400> SEQUENCE: 2

Xaa Arg Pro Tyr Asn Ala
1               5

<210> SEQ ID NO 3
<211> LENGTH: 6
<212> TYPE: PRT
<213> ORGANISM: Artificial sequence
<220> FEATURE:
<223> OTHER INFORMATION: synthetic peptide

<400> SEQUENCE: 3

Met Arg Pro Tyr Asp Ala
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Met Arg Pro Tyr Asp
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Gly Arg Pro Tyr
1

<210> SEQ ID NO 6
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Nle
```

```
<400> SEQUENCE: 6

Gly Xaa Arg Pro Tyr
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: 3,5-diiodotyrosine

<400> SEQUENCE: 7

Gly Xaa Arg Pro Xaa
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine

<400> SEQUENCE: 8

Gly Xaa Xaa Pro Tyr
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: 3,5-diiodotyrosine

<400> SEQUENCE: 9

Gly Xaa Xaa Pro Xaa
1               5

<210> SEQ ID NO 10
<211> LENGTH: 5
<212> TYPE: PRT
<213> ORGANISM: Artificial sequence
<220> FEATURE:
```

```
<223> OTHER INFORMATION: Synthetic peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
<223> OTHER INFORMATION: 4Hyp

<400> SEQUENCE: 10

Gly Xaa Xaa Xaa Tyr
1               5

<210> SEQ ID NO 11
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (4)..(4)
<223> OTHER INFORMATION: AMIDATION

<400> SEQUENCE: 11

Gly Arg Pro Tyr
1

<210> SEQ ID NO 12
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: AMIDATION

<400> SEQUENCE: 12

Gly Xaa Arg Pro Tyr
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
```

```
<223> OTHER INFORMATION: Nle
<220> FEATURE:
<221> NAME/KEY: MOD_RES
<222> LOCATION: (5)..(5)
<223> OTHER INFORMATION: AMIDATION
<220> FEATURE:
<221> NAME/KEY: MOD_RES
<222> LOCATION: (5)..(5)
<223> OTHER INFORMATION: 3,5-diiodotyrosine

<400> SEQUENCE: 13

Gly Xaa Arg Pro Xaa
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: AMIDATION

<400> SEQUENCE: 14

Gly Xaa Xaa Pro Tyr
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: 3,5-diiodotyrosine
<220> FEATURE:
<221> NAME/KEY: MOD_RES
<222> LOCATION: (5)..(5)
<223> OTHER INFORMATION: AMIDATION

<400> SEQUENCE: 15

Gly Xaa Xaa Pro Xaa
1               5

<210> SEQ ID NO 16
```

```
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
<223> OTHER INFORMATION: 4Hyp

<400> SEQUENCE: 16

Gly Xaa Xaa Xaa Tyr
1               5

<210> SEQ ID NO 17
<211> LENGTH: 11
<212> TYPE: PRT
<213> ORGANISM: Artificial sequence
<220> FEATURE:
<223> OTHER INFORMATION: Synthetic peptde

<400> SEQUENCE: 17

Ile Lys Met Arg Pro Tyr Asp Ala Asn Lys Arg
1               5                   10

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Met Arg Pro Tyr Asp Ala Asn Lys Arg
1               5

<210> SEQ ID NO 19
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Nle

<400> SEQUENCE: 19

Xaa Arg Pro Tyr
1

<210> SEQ ID NO 20
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: 3,5-diiodotyrosine

<400> SEQUENCE: 20

Xaa Arg Pro Xaa
1

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: homoarginine

<400> SEQUENCE: 21

Xaa Xaa Pro Tyr
1

<210> SEQ ID NO 22
<211> LENGTH: 4
<212> TYPE: PRT
<213> ORGANISM: Artificial sequence
<220> FEATURE:
<223> OTHER INFORMATION: Synthetic peptise
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: homoarginine
<220> FEATURE:
<221> NAME/KEY: MOD_RES
<222> LOCATION: (4)..(4)
<223> OTHER INFORMATION: 3,5-diiodotyrosine

<400> SEQUENCE: 22

Xaa Xaa Pro Xaa
1

<210> SEQ ID NO 23
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: homoarginine
<220> FEATURE:
<221> NAME/KEY: MOD_RES
<222> LOCATION: (3)..(3)
<223> OTHER INFORMATION: 4Hyp

<400> SEQUENCE: 23
```

```
Xaa Xaa Xaa Tyr
1

<210> SEQ ID NO 24
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 24

Gly Xaa Arg Pro Tyr Asn
1               5

<210> SEQ ID NO 25
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 25

Gly Arg Pro Tyr
1

<210> SEQ ID NO 26
<211> LENGTH: 7
<212> TYPE: PRT
<213> ORGANISM: Artificial sequence
<220> FEATURE:
<223> OTHER INFORMATION: synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (7)..(7)
<223> OTHER INFORMATION: DAla
<220> FEATURE:
<221> NAME/KEY: MOD_RES
<222> LOCATION: (7)..(7)
<223> OTHER INFORMATION: AMIDATION

<400> SEQUENCE: 26

Gly Xaa Arg Pro Tyr Asn Xaa
1               5
```

```
<210> SEQ ID NO 27
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (8)..(8)
<223> OTHER INFORMATION: coupled to fluorescein moiety
<220> FEATURE:
<221> NAME/KEY: MOD_RES
<222> LOCATION: (8)..(8)
<223> OTHER INFORMATION: AMIDATION

<400> SEQUENCE: 27

Gly Xaa Arg Pro Tyr Asn Ala Lys
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: 4-bromo-Phenylalanine

<400> SEQUENCE: 28

Gly Xaa Arg Pro Xaa
1               5

<210> SEQ ID NO 29
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Dodecanoyl
<220> FEATURE:
<221> NAME/KEY: MOD_RES
<222> LOCATION: (2)..(2)
<223> OTHER INFORMATION: Nle

<400> SEQUENCE: 29

Gly Xaa Arg Pro Tyr
1               5

<210> SEQ ID NO 30
<211> LENGTH: 5
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Decanoyl
<220> FEATURE:
<221> NAME/KEY: MOD_RES
<222> LOCATION: (2)..(2)
<223> OTHER INFORMATION: Nle

<400> SEQUENCE: 30

Gly Xaa Arg Pro Tyr
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Octanoyl
<220> FEATURE:
<221> NAME/KEY: MOD_RES
<222> LOCATION: (2)..(2)
<223> OTHER INFORMATION: Nle

<400> SEQUENCE: 31

Gly Xaa Arg Pro Tyr
1               5

<210> SEQ ID NO 32
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Hexanoyl
<220> FEATURE:
<221> NAME/KEY: MOD_RES
<222> LOCATION: (2)..(2)
<223> OTHER INFORMATION: Nle

<400> SEQUENCE: 32

Gly Xaa Arg Pro Tyr
1               5

<210> SEQ ID NO 33
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: 2-amino-3-guanidinopropionic acid
<220> FEATURE:
```

```
<221> NAME/KEY: MOD_RES
<222> LOCATION: (5)..(5)
<223> OTHER INFORMATION: AMIDATION

<400> SEQUENCE: 33

Gly Xaa Xaa Pro Tyr
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: citruline
<220> FEATURE:
<221> NAME/KEY: MOD_RES
<222> LOCATION: (5)..(5)
<223> OTHER INFORMATION: AMIDATION

<400> SEQUENCE: 34

Gly Xaa Xaa Pro Tyr
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: AMIDATION

<400> SEQUENCE: 35

Gly Xaa Lys Pro Tyr
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
```

```
<221> NAME/KEY: MOD_RES
<222> LOCATION: (5)..(5)
<223> OTHER INFORMATION: AMIDATION

<400> SEQUENCE: 36

Gly Xaa Gln Pro Tyr
1               5

<210> SEQ ID NO 37
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: AMIDATION

<400> SEQUENCE: 37

Xaa Xaa Xaa Pro Tyr
1               5

<210> SEQ ID NO 38
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: AMIDATION

<400> SEQUENCE: 38

Xaa Xaa Arg Pro Tyr
1               5

<210> SEQ ID NO 39
<211> LENGTH: 5
<212> TYPE: PRT
<213> ORGANISM: Artificial sequence
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: cholesteryl
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: OH group

<400> SEQUENCE: 39

Gly Xaa Xaa Pro Tyr
1               5

<210> SEQ ID NO 40
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: cholesteryl
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: OH group

<400> SEQUENCE: 40

Gly Xaa Arg Pro Tyr
1               5

<210> SEQ ID NO 41
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: ACYLATION

<400> SEQUENCE: 41

Gly Xaa Xaa Pro Tyr
1               5

<210> SEQ ID NO 42
<211> LENGTH: 5
<212> TYPE: PRT
```

```
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: ACYLATION

<400> SEQUENCE: 42

Gly Xaa Arg Pro Tyr
1               5

<210> SEQ ID NO 43
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: N-methyl norleucine
<220> FEATURE:
<221> NAME/KEY: MOD_RES
<222> LOCATION: (5)..(5)
<223> OTHER INFORMATION: AMIDATION

<400> SEQUENCE: 43

Gly Xaa Arg Pro Tyr
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: N-methyl arginine
<220> FEATURE:
<221> NAME/KEY: MOD_RES
<222> LOCATION: (5)..(5)
<223> OTHER INFORMATION: AMIDATION

<400> SEQUENCE: 44

Gly Xaa Xaa Pro Tyr
1               5

<210> SEQ ID NO 45
<211> LENGTH: 5
<212> TYPE: PRT
```

```
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: N-methyl norleucine
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: AMIDATION

<400> SEQUENCE: 45

Gly Xaa Xaa Pro Tyr
1               5

<210> SEQ ID NO 46
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
<223> OTHER INFORMATION: (S)-thiazolidine-2-carboxylic acid
<220> FEATURE:
<221> NAME/KEY: MOD_RES
<222> LOCATION: (5)..(5)
<223> OTHER INFORMATION: AMIDATION

<400> SEQUENCE: 46

Gly Xaa Xaa Xaa Tyr
1               5

<210> SEQ ID NO 47
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: (S)-thiazolidine-2-carboxylic acid
<220> FEATURE:
<221> NAME/KEY: MOD_RES
```

```
<222> LOCATION: (5)..(5)
<223> OTHER INFORMATION: AMIDATION

<400> SEQUENCE: 47

Gly Xaa Arg Xaa Tyr
1               5

<210> SEQ ID NO 48
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 48

Gly Xaa Xaa Xaa Tyr
1               5

<210> SEQ ID NO 49
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
<223> OTHER INFORMATION: 3Hyp
<220> FEATURE:
<221> NAME/KEY: MOD_RES
<222> LOCATION: (5)..(5)
<223> OTHER INFORMATION: AMIDATION

<400> SEQUENCE: 49

Gly Xaa Xaa Xaa Tyr
1               5

<210> SEQ ID NO 50
<211> LENGTH: 5
<212> TYPE: PRT
<213> ORGANISM: Artificial sequence
```

```
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 50

Gly Xaa Arg Xaa Tyr
1               5

<210> SEQ ID NO 51
<211> LENGTH: 5
<212> TYPE: PRT
<213> ORGANISM: Artificial sequence
<220> FEATURE:
<223> OTHER INFORMATION: synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: 3Hyp
<220> FEATURE:
<221> NAME/KEY: MOD_RES
<222> LOCATION: (5)..(5)
<223> OTHER INFORMATION: AMIDATION

<400> SEQUENCE: 51

Gly Xaa Arg Xaa Tyr
1               5

<210> SEQ ID NO 52
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
<223> OTHER INFORMATION: (2S,3aS,7aS) Octahydro-1H-indole-2-carboxylic
      acid
<220> FEATURE:
<221> NAME/KEY: MOD_RES
```

-continued

```
<222> LOCATION: (5)..(5)
<223> OTHER INFORMATION: AMIDATION

<400> SEQUENCE: 52

Gly Xaa Xaa Xaa Tyr
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: (2S,3aS,7aS) Octahydro-1H-indole-2-carboxylic
      acid
<220> FEATURE:
<221> NAME/KEY: MOD_RES
<222> LOCATION: (5)..(5)
<223> OTHER INFORMATION: AMIDATION

<400> SEQUENCE: 53

Gly Xaa Arg Xaa Tyr
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: (4-NH2) Phenylalanine
<220> FEATURE:
<221> NAME/KEY: MOD_RES
<222> LOCATION: (5)..(5)
<223> OTHER INFORMATION: AMIDATION

<400> SEQUENCE: 54

Gly Xaa Arg Pro Xaa
1               5

<210> SEQ ID NO 55
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: LIPID
<222> LOCATION: (1)..(1)
<223> OTHER INFORMATION: MYRISTATE
<220> FEATURE:
```

```
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: (4-NH2) Phenylalanine
<220> FEATURE:
<221> NAME/KEY: MOD_RES
<222> LOCATION: (5)..(5)
<223> OTHER INFORMATION: AMIDATION

<400> SEQUENCE: 55

Gly Xaa Xaa Pro Xaa
1               5

<210> SEQ ID NO 56
<211> LENGTH: 5
<212> TYPE: PRT
<213> ORGANISM: Artificial sequence
<220> FEATURE:
<223> OTHER INFORMATION: synthetic peptide
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (5)..(5)
<223> OTHER INFORMATION: (3,5-diiodo)tyrosine
<220> FEATURE:
<221> NAME/KEY: MOD_RES
<222> LOCATION: (5)..(5)
<223> OTHER INFORMATION: AMIDATION

<400> SEQUENCE: 56

Gly Xaa Xaa Pro Xaa
1               5
```